US010995124B2

(12) United States Patent
Berezina et al.

(10) Patent No.: US 10,995,124 B2
(45) Date of Patent: May 4, 2021

(54) CHITIN, HYDROLYSATE AND PRODUCTION OF AT LEAST ONE DESIRED PRODUCT FROM INSECTS BY MEANS OF ENZYMATIC HYDROLYSIS, COMPRISING A COMBINATION OF STEPS PERFORMED PRIOR TO THE ENZYMATIC HYDROLYSIS

(71) Applicant: YNSECT, Evry (FR)

(72) Inventors: Nathalie Berezina, Paris (FR); Antoine Hubert, Alfortville (FR); Fabrice Berro, Paris (FR); Jean-Gabriel Levon, Paris (FR); Karine Le Roux, Milly la Foret (FR); Cecilia Socolsky, Paris (FR); Lorena Sanchez, Juvisy (FR); Sophie Laurent, Paris (FR)

(73) Assignee: YNSECT, Evry (FR)

( * ) Notice: Subject to any disclaimer, the term of this patent is extended or adjusted under 35 U.S.C. 154(b) by 174 days.

(21) Appl. No.: 15/541,162

(22) PCT Filed: Dec. 30, 2015

(86) PCT No.: PCT/FR2015/053783
§ 371 (c)(1),
(2) Date: Jun. 30, 2017

(87) PCT Pub. No.: WO2016/108035
PCT Pub. Date: Jul. 7, 2016

(65) Prior Publication Data
US 2019/0153046 A1 May 23, 2019

(30) Foreign Application Priority Data

Dec. 31, 2014 (FR) ...................... 1463513

(51) Int. Cl.
| C07K 14/435 | (2006.01) |
| C08B 37/08 | (2006.01) |
| C12P 19/26 | (2006.01) |
| C12P 21/06 | (2006.01) |
| C08B 37/00 | (2006.01) |
| C08L 5/08 | (2006.01) |

(52) U.S. Cl.
CPC ...... *C07K 14/43563* (2013.01); *C08B 37/003* (2013.01); *C08B 37/0003* (2013.01); *C08L 5/08* (2013.01); *C12P 19/26* (2013.01); *C12P 21/06* (2013.01)

(58) Field of Classification Search
CPC ... C08B 37/003; C08B 37/0003; A23K 50/90; A61K 8/736; C11B 1/10; C07K 14/43563; C08L 5/08; C12P 21/06
See application file for complete search history.

(56) References Cited

U.S. PATENT DOCUMENTS

| 4,958,011 A | 9/1990 | Bade |
| 2003/0233982 A1 | 12/2003 | Zhang |

FOREIGN PATENT DOCUMENTS

| CN | 1297691 | 6/2001 |
| CN | 1415757 | 5/2003 |
| CN | 101078023 | 11/2007 |
| CN | 101144197 | 3/2008 |
| CN | 101775085 | 7/2010 |
| CN | 101880591 | 11/2010 |
| CN | 101144097 | 12/2010 |
| CN | 102048020 | 5/2011 |
| CN | 102199228 | 9/2011 |
| CN | 102342394 | 2/2012 |
| CN | 102558387 | 7/2012 |
| CN | 102578361 | 7/2012 |
| CN | 103694372 | 4/2014 |
| FR | 2927336 | 8/2009 |
| JP | 2009254348 | 11/2009 |
| RU | 2345139 | 1/2009 |
| WO | WO 2004049818 | 6/2004 |
| WO | WO 2012/168618 | 12/2012 |
| WO | WO 2013/191548 | 12/2013 |

OTHER PUBLICATIONS

FAO. Processing edible insects for food and feed, www.fao.org. 2009;107-115.*
Brück et al., *Chitin and Chitosan from Marine Organisms*, Chitin and Chitosan and Their Derivatives Biological Activities and Applications, 11-23 (2010).
Dai et al., *Angiotensin I-converting enzyme (ACE) inhibitory peptide derived from Tenebrio molitor (L.) larva protein hydrolysate*, 236 Eur Food Res Technol 681-689 (2013).
Gortari et al., *Biotechnological processes for chitin recovery out of crustacean waste: A mini-review*, Electronic Journal of Biotechnology 1-18 (May 15, 2013).
Manni et al., *An Oxidant—and Solvent-Stable Protease Produced by Bacillus cereus SV1: Application in the Deproteinization of Shrimp Wastes and as a Laundry Detergent Additive*, 160 App. Biochem. Bitotechnol 2308-2321 (2010).
Nwe et al., *Chitin and Chitosan from Terrestrial Organisms*, Chitin and Chitosan and Their Derivatives Biological Activities and Applications, 3-10 (2010).
Wang et al., *Housefly larvae hydrolysate: orthogonal optimization of hydrolysis, antioxidant activity, amino acid compositions and functional properties*, 6 BMC Research 1-10 (2013).

(Continued)

*Primary Examiner* — Lynn Y Fan
(74) *Attorney, Agent, or Firm* — Panitch Schwarze Belisario & Nadel LLP

(57) ABSTRACT

The invention relates to a method for the production of chitin and/or chitosan from insects. More specifically, the invention relates to a method for the production of chitin and/or chitosan from insect cuticles, comprising an insect cuticle pressing step, followed by a step involving the enzymatic hydrolysis of the insect cuticles using a proteolytic enzyme, the cuticles having been treated with an oxidising agent prior to the enzymatic hydrolysis.

13 Claims, 16 Drawing Sheets

(56) References Cited

OTHER PUBLICATIONS

Figure 1:
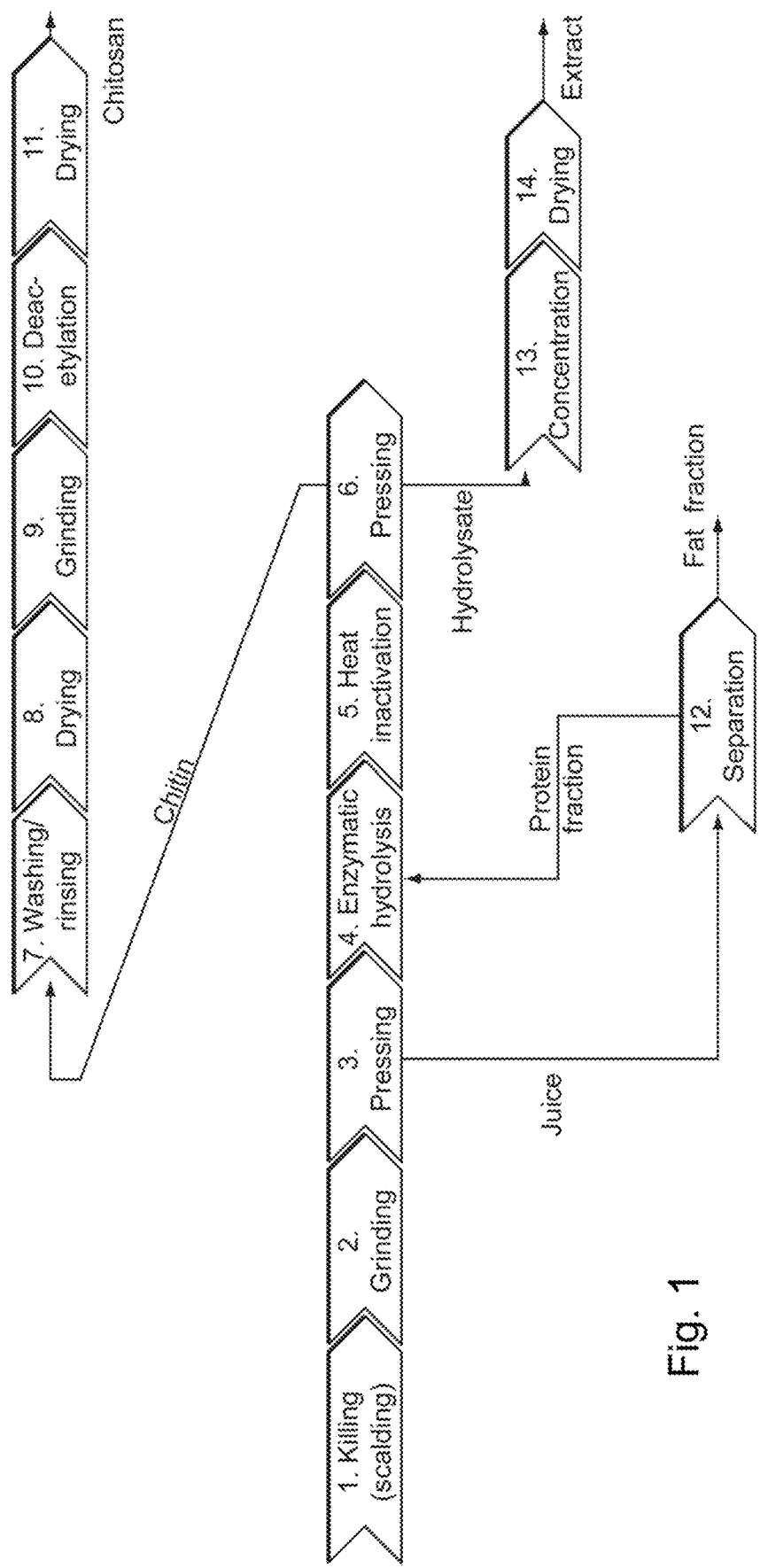

Bukkens, *The Nutritional Value of Edible Insects*, 36 Ecology of Food and Nutrition 287-319 (1997).
Dreyer et al., *On the Nutritive Value of Mopanie Worms*, 78 South African Journal of Science 33-35 (Jan. 1982).
Gutierrez et al., *Análisis Composicional, Microbiológico y Digestibilidad de la Proteína de la Harina de Larvas de Hermetia illuscens L (Diptera:Stratiomyiidae) en Angelópolis-Antioquia, Colombia*, 57(2) Rev. Fac. Nac. Agron. Medellin 2491-2499 (2004) (English abstract provided).
Iñiguez-Covarrubias et al., *Biodegradation of Swine Waste by House-Fly Larvae and Evaluation of Their Protein Quality in Rats*, 6(1) Journal of Applied Animal Research 65-74 (1994).
Kroeckel et al., *When a turbot catches a fly: Evaluation of a pre-pupae meal of the Black Soldier Fly (Hermetia illucens) as fish meal substitute—Growth performance and chitin degradation in juvenile turbot (Psetta maxima)*, 364-365 Aquaculture 345-352 (2012).
Pretorius, *The Evaluation of Larvae of Musca Domestica (Common House Fly) as Protein Source for Broiler Production*, Master Thesis, Stellenbosch University (entire thesis) (Mar. 2011).
Ramos-Elorduy de Concone et al., *Digestibilidad* in vitro *de Algunos Insectos Comestibles en Mexico*, 49 Folia Entomologica Mexicana 141-154 (1981).
Vedlkamp et al., *Insects as sustainable feed ingredient in pig and poultry diets—a feasibility study*, Report 638 Livestock Research Wageningen UR (Oct. 2012).
St-Hilaire et al., *Fish Offal Recycling by the Black Soldier Fly Produces a Foodstuff High in Omega-3 Fatty Acids*, 38(2) Journal of the World Aquaculture Society 309-313 (2007).
Tajik et al., *Preparation of Chitosan from Brine Shrimp (Artemia urminana) Cyst Shells and Effects of Different Chemical Processing Sequences on the Physicochemical and Functional Properties of the Product*, 13 Molecules 1263-1274 (2008).

\* cited by examiner

■ purity of the chitin
● lipid content in the hydrolysate
◇ lipid content in the chitin

CHITIN, HYDROLYSATE AND PRODUCTION OF AT LEAST ONE DESIRED PRODUCT FROM INSECTS BY MEANS OF ENZYMATIC HYDROLYSIS, COMPRISING A COMBINATION OF STEPS PERFORMED PRIOR TO THE ENZYMATIC HYDROLYSIS

CROSS-REFERENCE TO RELATED APPLICATIONS

This application is a U.S. National Stage Application pursuant to 35 U.S.C. § 371 of International Patent Application PCT/FR2015/053783, filed on Dec. 30, 2015, and published as WO 2016/108035 on Jul. 7, 2016, which claims priority to French Patent Application 1463513, filed on Dec. 31, 2014, all of which are incorporated herein by reference in their entireties for all purposes.

The present invention relates to a method for preparing at least one product of interest, and more particularly chitin and/or chitosan from insects. More particularly, the invention relates to a method for preparing chitin and/or chitosan by means of enzymatic hydrolysis of insect cuticles. It also relates to a specific chitin and a hydrolysate.

According to the invention, by "chitin" is meant any type of chitin derivative, i.e. any type of polysaccharide derivative comprising N-acetylglucosamine units and D-glucosamine units, in particular the chitin-polypeptide copolymers (sometimes referred to as "chitin/polypeptide composite").

Chitin is said to be the second most synthesized polymer in the living world after cellulose. In fact, chitin is synthesized by many species in the living world: it constitutes part of the exoskeleton of crustaceans and insects and the lateral wall which surrounds and protects fungi. More particularly, in insects, chitin thus constitutes 3 to 60% of their exoskeleton.

By "chitosan" is meant, according to the present invention, the products of the deacetylation of chitin. The usual limit between chitosan and chitin is determined by the degree of acetylation: a compound having a degree of acetylation less than 50% is called chitosan, and a compound having a degree of acetylation greater than 50% is called chitin.

Chitin and/or chitosan are used in numerous applications: cosmetic (cosmetic composition), medical and pharmaceutical (pharmaceutical composition, treatment of burns, biomaterials, corneal dressings, suture material), dietetics and food processing, technical (filtering, texturizing, flocculating or adsorbent agents in particular for water filtration and purification), etc. In fact, chitin and/or chitosan are materials that are biocompatible, biodegradable and non-toxic.

Traditionally, chitin is extracted chemically from crustaceans, from cephalopods, but also, more exceptionally, from fungi. The chemical route uses large quantities of reagents (such as hydrochloric acid, sodium hydroxide and bleaching agents), which have the effect of denaturing the structure of chitin such as it exists in the natural state, for example as present in the shell of crustaceans. Moreover, most of the chemical reagents are harmful to humans and the environment and generate large volumes of effluents that have to be treated. Finally, chitin and/or chitosan originating from crustaceans can generate allergic reactions in sensitive persons.

Another route for extraction of chitin is the enzymatic route. This route is considered to be milder, thus making it possible to better preserve the chitin and/or chitosan. However, the chitin obtained by this route is of a brownish colour, requiring purification steps in order to obtain a marketable powder, i.e. of white colour. The existing methods therefore generally comprise one or more steps for removing the impurities from chitin, such as a step of demineralization with acid, carried out prior to enzymatic hydrolysis, and/or a step of bleaching the chitin with an oxidizing agent, carried out after enzymatic hydrolysis. These two steps for the purification of chitin unfortunately have the effect of altering the chemical structure of chitin.

Work undertaken by the inventors demonstrated that it was possible to obtain chitin that is both purer and has a structure closer to the original structure of chitin by carrying out a specific combination of steps prior to hydrolysis, namely a pressing step and a step of treating the insect cuticles with an oxidizing agent.

The invention therefore relates to a method for the production of chitin and/or chitosan from insect cuticles, comprising the following steps:

(i) pressing insect cuticles, then, (ii) enzymatic hydrolysis of the insect cuticles with a proteolytic enzyme, a treatment of the cuticles with an oxidizing agent having been carried out prior to enzymatic hydrolysis.

By "insects" is meant insects at any stage of development, such as an adult, larval or nymph stage. Preferably, the insects used in the method according to the invention are edible.

More particularly, the insects can be selected from the group constituted by the Coleoptera, Diptera, Lepidoptera, Isoptera, Orthoptera, Hymenoptera, Blattoptera, Hemiptera, Heteroptera, Ephemeroptera and Mecoptera, preferably from the Coleoptera, Diptera, Orthoptera and Lepidoptera.

Preferably, the insects are selected from the group constituted by *Tenebrio molitor, Hermetia illucens, Galleria mellonella, Alphitobius diaperinus, Zophobas morio, Blattera fusca, Tribolium castaneum, Rhynchophorus ferrugineus, Musca domestica, Chrysomya megacephala, Locusta migratoria, Schistocerca gregaria, Acheta domesticus* and *Samia ricini*.

More preferably, the insects are selected from the group constituted by *Tenebrio molitor, Hermetia illucens, Galleria mellonella, Alphitobius diaperinus, Zophobas morio, Blattera fusca, Musca domestica, Chrysomya megacephala, Locusta migratoria, Schistocerca gregaria, Acheta domesticus* and *Samia ricini*, and even more preferably, *T. molitor*.

One or more insect species can be used in the method according to the invention, preferably a single insect species. If several species are used, advantageously two closely related species will be selected, for example *Hermetia illucens* and *Musca domestica*.

The insects are preferably reared, rather than taken from nature. For example, the insects are reared in an insect farm. Breeding the insects in a special farm makes it possible not only to control and eliminate the risks associated with insect-borne diseases, but also to limit the risks associated with the toxicity of food products derived from insects due for example to the presence of insecticides. Moreover, farming makes it possible to control the quality of the supply of insects and limit the costs of supply.

By "insect cuticles" is meant not only the cuticles once they have been separated from the insects, but also the cuticles including some or all of the other constituents of the insect, including the whole insect. In fact, it is possible to apply the method according to the invention to the whole insect, such as ground insects, or only to a part of the insects comprising the cuticles, for example the exuviae and/or the molts of insects, separated naturally and collected by a suitable method.

The cuticle is the outer layer (or exoskeleton) secreted by the epidermis of the insects. Generally it is formed from three layers:
- the epicuticle, which is the thinnest, outermost layer of the cuticle (less than 4 µm); this layer is impermeable to water and comprises a layer of water-repelling wax, as well as a smaller amount of proteins and chitin;
- the exocuticle, which is the intermediate layer of the cuticle; it consists essentially of proteins that have been hardened by tanning, and are responsible for the rigidity of the cuticle, chitin, and optionally melanin; and
- the endocuticle, which is a thin, flexible layer, constituted by a mixture of proteins and chitin.

The main objective of pressing insect cuticles is to remove a fat-rich press juice and/or to enrich the press cake to give a substrate for hydrolysis.

In the method according to the invention, pressing the insect cuticles makes it possible to obtain a press cake comprising an oil (or lipids) content less than or equal to 20%, preferably less than or equal to 15%, more preferably less than or equal to 12%, even more preferably less than or equal to 10%.

In the present application, the ranges of values are understood to be inclusive. Moreover, when "approximately" or "of the order of" precedes a number, this is equivalent to plus or minus 10% of the value of this number.

Likewise, in order to enrich the press cake into a substrate for hydrolysis, pressing the insect cuticles makes it possible to obtain a press cake having a dry matter content comprised between 30% and 60%, preferably comprised between 40% and 55%, and more preferably comprised between 45% and 50%.

Any press system can be used for carrying out the pressing of the insect cuticles, for example a single-screw or twin-screw press (twin-screw press of the Angel type), a filter-press (filter-press of the Choquenet type), a platen press, etc. These systems are well known to a person skilled in the art, who is able to determine the pressing conditions so as to obtain the contents of oil and/or of water mentioned above.

In the method according to the invention, pressing the insect cuticles is followed by enzymatic hydrolysis.

Preferably, enzymatic hydrolysis is carried out with at least one proteolytic enzyme, preferably a protease. In the present application, the names or suffixes "peptidase" and "protease" are used indiscriminately to denote an enzyme causing lysis of a peptide bond of the proteins. Advantageously, this is carried out for a time of from 4 to 8 h, preferably for 4 to 5 h, at a temperature from 40 to 60° C., preferably 45 to 55° C. and at a pH comprised between 6 and 8, preferably between 6.5 and 7.5.

Enzymatic hydrolysis can be carried out with a single protease or alternatively with a mixture of enzymes containing at least one protease, more preferably a mixture of enzymes containing several proteases, such as a mixture containing an endoprotease and an exoprotease, or a protease and a polysaccharase.

Preferably, the protease is selected from the group constituted by the aminopeptidases, metallocarboxypeptidases, serine endopeptidases, cysteine endopeptidases, aspartic endopeptidases, metalloendopeptidases.

Advantageously, the enzymes can be selected from the following:

| Enzyme(s) | Class | EC number | Supplier | Town | Country |
|---|---|---|---|---|---|
| Flavourzyme | Amino-peptidases | EC 3.4.11.1 | Novozyme | Bagsvaerd | Denmark |
| Fungal protease 500 | | EC 3.4.11.1 | BioCat | Troy | United States |
| Kojizyme | | EC 3.4.11.1 | Novozyme | Bagsvaerd | Denmark |
| Protex P | Serine endopeptidases | EC 3.4.21 | Genencor International B.V. | Leiden | The Netherlands |
| Chymotrypsin | | EC 3.4.21.1 | Novozyme | Bagsvaerd | Denmark |
| Protamex | | EC 3.4.21 | Novozyme | Bagsvaerd | Denmark |
| Elastase | | EC 3.4.21.14 | Novozyme | Bagsvaerd | Denmark |
| Trypsin | | EC 3.4.21.36 | Novozyme | Bagsvaerd | Denmark |
| Alcalase | | EC 3.4.21.4 | Novozyme | Bagsvaerd | Denmark |
| Papain | Cysteine endopeptidases | EC 3.4.22.2 | BioCat | Troy | United States |
| Bromelain (ananase) | | EC 3.4.22.32 | BioCat | Troy | United States |
| Prolyve NP | Aspartic endopeptidases | EC 3.4.23 | Lyven | Colombelles | France |
| Pepsin | | EC 3.4.23.1 | Sigma Aldrich | Saint-Quentin-Fallavier | France |
| Neutral protease | Metallo-endopeptidase | EC 3.4.24.28 | BioCat | Troy | United States |
| Protex 50FP | Endopeptidase | EC 3.4.21 | Genencor International B.V. | Leiden | The Netherlands |
| Pancrealyve | Exo & endo peptidase (cocktail of proteases + amylases) | n.a.* | Lyven | Colombelles | France |

-continued

| Enzyme(s) | Class | EC number | Supplier | Town | Country |
|---|---|---|---|---|---|
| lzyme BA | Aspartic protease | EC 3.4.23 | Novozyme | Bagsvaerd | Denmark |
| Sumizyme | Enzyme cocktail | n.a.* | Takabio - Shin Nihon | Aichi | Japan |
| Neutrase | Endoprotease Zn base of β amyloliquefaciens | EC 3.4.24 | Novozyme | Bagsvaerd | Denmark |
| Novozyme 37071 | Protease | n.a.* | Novozyme | Bagsvaerd | Denmark |

*n.a.: not applicable

Advantageously, the enzyme used in the hydrolysis is an aspartic endopeptidase, such as Prolyve NP. This type of enzyme makes it possible to obtain very good results in terms of purity of the chitin obtained, especially when this type of enzyme is applied in the hydrolysis of a press cake obtained from Coleoptera and more particularly from *T. molitor*.

The enzyme or the mixture of enzymes is introduced in a quantity ranging from 0.2 to 10% by weight of estimated dry matter, preferably from 0.4 to 8% by weight and more preferably from 0.5 to 2%. By "weight of estimated dry matter" is meant more particularly the weight of dry matter from insects or insect part(s), such as can be estimated when entering the enzymatic hydrolysis step.

In terms of enzymatic activity, the quantity of enzyme or enzyme mixture introduced is equivalent to an activity comprised between 2000 and 5000 SAPU ("Spectrophotometric Acid Protease Unit", described in Example 5 below), preferably between 3000 and 4000 SAPU, per 100 g wet weight, with a water content from 30 to 70%, of substrate to be transformed, i.e. of insect or hydrated insect part(s).

Advantageously, the enzymatic hydrolysis step is carried out in the presence of water, such as fresh water. The quantity of water used in the enzymatic hydrolysis is determined as follows: the ratio of the volume of water in mL to the weight of insect in g is preferably comprised between 0.3 and 10, more preferably between 0.5 and 5, even more preferably between 0.7 and 3, even more preferably of the order of 1. It should be noted that this ratio also corresponds to the ratio of the weight of water to the weight of insect material, the density of water being 1.0 g/mL under normal temperature and pressure conditions.

In the method according to the invention, enzymatic hydrolysis is preceded by a step of treating the cuticles with an oxidizing agent.

Preferably, in the method according to the invention, the oxidizing agent used for treating the cuticles is selected from the group constituted by hydrogen peroxide, potassium permanganate, ozone and sodium hypochlorite, even more preferably hydrogen peroxide.

Advantageously, when the oxidizing agent is hydrogen peroxide, the quantity of this agent used for treating the insect cuticles is such that the hydrogen peroxide content is comprised between 1 and 33% by weight based on the total weight of insects, preferably comprised between 2 and 12% by weight based on the total weight of insects, preferably of the order of 6% by weight.

Preferably, treatment of the insect cuticles with the oxidizing agent is carried out in the presence of water, such as fresh water. Advantageously, the quantity of water used in the treatment of the cuticles is determined as follows: the ratio of the volume of water in mL to the weight of insect in g is preferably comprised between 0.3 and 10, more preferably between 0.5 and 5, even more preferably between 0.7 and 3, even more preferably of the order of 1.

Figure 7:
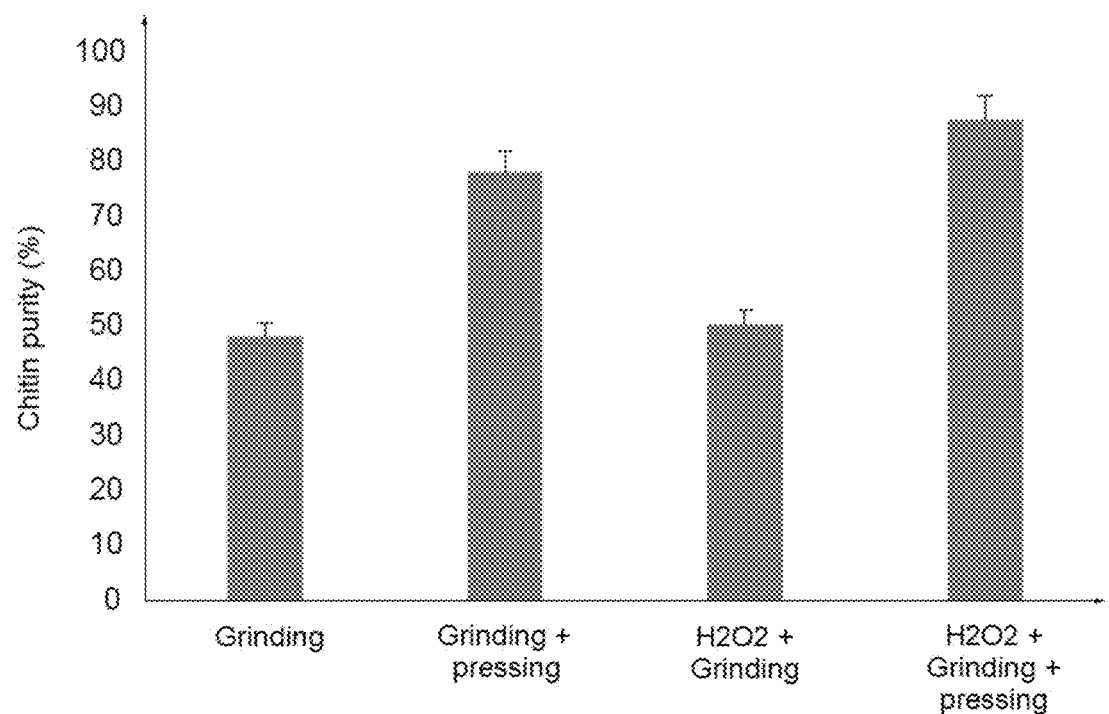

The method according to the invention makes it possible to obtain a chitin having a high degree of purity, such as a degree of purity (or gravimetric purity) comprised between 55 and 95%, preferably comprised between 60 and 95%, even more preferably between 70 and 90%, and even more preferably between 80 and 90% (see Example 5 and FIG. 7).

Preferably, the method according to the invention comprises a grinding step prior to the pressing step.

This grinding step has the objective of reducing the cuticles and/or the insects to particles in order to facilitate access of the enzymes to the substrate during enzymatic hydrolysis. This step also makes it possible, when it is followed by a pressing step, to facilitate removal of the press juice and isolation of the solid matter.

Grinding can advantageously be carried out with a mixer-grinder, such as a knife mill.

Preferably, at the end of grinding, the size of the particles of insect is less than 1 cm (largest particle size observable using a microscope), preferably less than 0.5 cm, even more preferably a size comprised between 300 μm and 0.5 cm, more preferably 500 μm and 0.5 cm and even more preferably between 500 μm and 1 mm.

A quantity of water can be added to facilitate grinding. This quantity of water is determined as follows: the ratio of the volume of water in mL to the weight of insect in g is preferably comprised between 0.3 and 10, more preferably between 0.5 and 5, even more preferably between 0.7 and 3, even more preferably of the order of 1.

Advantageously, in the method according to the invention, the treatment of the cuticles with an oxidizing agent is carried out before, concomitantly and/or after the grinding and/or pressing step.

The method according to the invention can also comprise a step of killing the insects prior to the pressing and/or grinding step.

This killing step can be carried out by conventional methods in the farming of cold-blooded animals and/or animals of small size (crustaceans, fish, snails, etc.), such as cold (freezing), heat (scalding), oxygen deprivation, etc. Advantageously, the insect killing step is carried out by scalding. Scalding not only kills the insects, but also lowers the microbial load (reducing the risk of deterioration and health risk) and inactivates the internal enzymes of the insects which can trigger autolysis, and thus a rapid browning thereof. This scalding is carried out in such a way as to cause death as quickly as possible, in order to respect animal welfare, and according to scientific recommendations.

Alternatively, killing can be carried out by blanching. Blanching has the same advantages as scalding as mentioned above.

Advantageously, the insects are killed, for example by scalding or blanching, and then ground before being pressed.

Preferably, the scalding step is carried out in water, such as fresh water, at a temperature from 95 to 105° C., preferably of the order of 100° C. and for a time from 2 to 20 min, preferably 5 to 15 min.

The quantity of water introduced in this scalding step is determined as follows: the ratio of the volume of water in mL to the weight of insect in g is preferably comprised between 0.3 and 10, more preferably between 0.5 and 5, even more preferably between 0.7 and 3, even more preferably of the order of 1.

Alternatively, the blanching step is carried out with steam and/or with water at a temperature comprised between 80° C. and 130° C., preferably between 90° C. and 120° C.

Advantageously, the treatment of the cuticles with an oxidizing agent is carried out concomitantly and/or after the killing step and in particular concomitantly and/or after scalding.

More particularly, the treatment of the insect cuticles with the oxidizing agent can be carried out during one or more of the following steps:
  concomitantly with scalding and/or after the scalding step, more preferably concomitantly with scalding, alternatively concomitantly with blanching and/or after the blanching step, more preferably concomitantly with blanching. More particularly, when the treatment of the insect cuticles is carried out during scalding, the oxidizing agent can advantageously be added to the water used for scalding the insects.
  before, concomitantly and/or after grinding. More particularly, when treatment of the insect cuticles is carried out during grinding, the oxidizing agent can advantageously be added to the water used for grinding.
  before and/or concomitantly with pressing.
  during a special step of treatment of the insect cuticles.

After enzymatic hydrolysis, the method according to the invention can further comprise a thermal inactivation step with the aim of inactivating the enzyme or the mixture of enzymes used in enzymatic hydrolysis.

At the end of a method according to the invention, the chitin can be recovered by pressing or centrifugation of the enzymatic hydrolysis reaction mixture. At this stage, a chitin co-product of interest is also recovered, namely a hydrolysate.

By "hydrolysate" is meant a product that comprises proteins, hydrolysed proteins, peptides, amino acids and/or other compounds derived from a protein, obtainable by enzymatic hydrolysis of proteins.

The invention also relates to a hydrolysate, such as a hydrolysate obtainable as a co-product of enzymatic hydrolysis by any one of the methods according to the invention.

The hydrolysate according to the invention has at least any one of the following characteristics:
  Ash content ≤3.5% by weight based on the total weight of dry matter,
  Ash content ≤2.5% when the hydrolysate is prepared from vegetarian insects,
  Content of water-soluble proteins of size >12,400 g/mol, 20%, preferably <18% by weight, based on the total weight of water-soluble proteins,
  Protein content ≥70%, preferably ≥74%,
  Protein content ≥80% when the hydrolysate is prepared from non-flying insects,
  Lipid content ≤0% by weight based on the total weight of dry matter,
  Lipid content ≤4.5% when the hydrolysate is prepared from non-flying insects,
  Pepsin digestibility >93% relative to the total weight of proteins,
  Relative abundance of at least any 5 amino acids selected from ASP, GLU, ALA, GLY, LEU, PRO, TYR, VAL, LYS 6%,
  Relative abundance of at least any 3 amino acids selected from ASP, GLU, ALA, LEU, PRO, TYR, VAL ≥8%.

By "vegetarian insect" is meant an insect that does not have animal proteins in its usual diet. By way of an example of vegetarian insects, Coleoptera, Lepidoptera or Orthoptera may be mentioned.

By "flying insect" is meant an insect that is capable of flying when adult, in contrast to an insect called "non-flying". By way of an example of flying insects, the Lepidoptera or Diptera may be mentioned. By way of an example of non-flying insects, certain Coleoptera or Orthoptera may be mentioned.

More particularly, by "water-soluble proteins" is meant, among the proteins (or crude proteins), those that are soluble in an aqueous solution the pH of which is comprised between 6 and 8, advantageously between 7.2 and 7.6.

Preferably, the aqueous solution is a buffer solution the pH of which is comprised between 6 and 8, advantageously between 7.2 and 7.6.

Preferably, the buffer solution is a phosphate buffered NaCl solution, the pH of which is equal to 7.4±0.2.

More particularly, the size of the water-soluble proteins is measured by the following method:

100 mg of sample was introduced into 10 mL of phosphate/NaCl buffer (pH 7.4, 0.137 mM). The sample was stirred for one minute (vortex), centrifuged at 900 g for 1 min and then filtered through a 0.45 μm membrane. The analysis was carried out on a steric exclusion chromatography system, with the Nucleogel GFC-300 column, the eluent used is phosphate/NaCl buffer (pH 7.4, 0.137 mM), the flow rate is 1.0 mL/min, with detection by a UV detector at 280 nm.

Advantageously, the hydrolysate comprises at least 70%, preferably at least 74% proteins, at most 3.5% ash and a content of water-soluble proteins having a size greater than 12,400 g/mol, less than 20%, preferably less than 18%.

Preferably, the hydrolysate has all the above properties.

It will be noted in particular that the hydrolysate according to the invention can be distinguished from any other type of hydrolysate by its glucosamine content, and/or a derivative thereof (preferably N-acetylglucosamine), more particularly a content greater than or equal to 0.01%, preferably greater than or equal to 0.08% by weight based on the total weight of dry matter of the hydrolysate.

All the units and methods of measurement of the characteristics stated above are described in the examples and, more particularly, in Example 6.

This hydrolysate can advantageously be supplemented with additives for balancing its nutritional profile so that it is suitable for different types of animals.

The hydrolysate can be concentrated and then dried to obtain a dried hydrolysate. Alternatively, the hydrolysate can be in liquid form. These hydrolysates can be used as a foodstuff or a food ingredient in particular for animals, or alternatively they can be treated, for example to isolate amino acids.

A preferred embodiment of a method according to the invention is described in more detail below.

In particular, this preferred embodiment describes various advantageous steps for a method according to the invention, such as steps of mild purification of the chitin: a second pressing, washing operations, optional filtration and drying.

Finally, as chitin is generally marketed in the form of powder, a second grinding can also be carried out. The latter can also be carried out to promote the deacetylation reaction, for preparing chitosan from chitin. The conditions of the deacetylation reaction are described more fully in step 10 of the preferred embodiment described in detail below.

The chitin according to the invention has at least any one of the following properties:

Ash content ≤3%, preferably ≤2.5% by weight based on the total weight of dry matter,
Ash content ≤1% when the chitin is prepared from *T. molitor*,
Lipid content ≤6.5% by weight based on the total weight of dry matter,
Lipid content ≤2% when the chitin is prepared from *T. molitor*,
Total amino acids ≤50%, preferably ≤46%,
Total amino acids ≤19% when the chitin is prepared from flying insects,
Amino acid content ≤23% when the chitin is prepared from *T. molitor* with Prolyve NP as enzyme,
Relative abundance of at least any 3 amino acids, selected from ALA, GLY, LEU, PRO, SER, TYR, VAL ≤10%,
Relative abundance of LEU, PRO, VAL ≤10%, when the chitin is prepared from *T. molitor*,
Colorimetric purity ≥62%,
Purity by difference ≥1.0%, preferably ≥46%,
Purity by difference ≥51% when the chitin is prepared from *T. molitor*,
Purity by difference ≥73% when the chitin is prepared from flying insects,
Purity by difference ≥73% when the chitin is prepared from *T. molitor* with Prolyve NP.

The chitin according to the invention advantageously comprises an amino acid content less than or equal to 50%, preferably less than or equal to 46%, an ash content less than or equal to 3%, preferably less than or equal to 2.5%, and a purity by difference greater than or equal to 40%, preferably greater than or equal to 46%.

Preferably, the chitin has all the above properties.

All the units and methods of measurement of the features stated above are described in the examples, and more particularly in Example 6.

A particularly advantageous method for the production of chitin from insects comprises the following steps:
a) killing the insects,
b) grinding the insects,
c) pressing the insects,
d) enzymatic hydrolysis of the insect cuticles with a proteolytic enzyme,
e) recovery of the chitin,
the insect cuticles being treated with an oxidizing agent before step d).

The preferred embodiments of the various steps a) to e) and the treatment of the insect cuticles with an oxidizing agent are as stated above or in the corresponding step in the preferred embodiment below.

The invention also relates to a chitin, such as a chitin obtainable by a method according to the invention. Owing to the mild conditions used in the method according to the invention, this chitin has a structure close to that of the chitin as it occurs in the natural state in the insect cuticle while having a high degree of purity, such as a degree of purity comprised between 55 and 95%, preferably comprised between 60 and 95%, even more preferably between 70 and 90%, and even more preferably between 80 and 90%.

A particularly advantageous method for the production of chitosan from insects, comprising the following steps:
a) killing the insects,
b) grinding the insects,
c) pressing the insects,
d) enzymatic hydrolysis of the insect cuticles with a proteolytic enzyme,
e) recovery of the chitin,
f) deacetylation of the chitin recovered,
g) recovery of the chitosan,
the insect cuticles being treated with an oxidizing agent before step d).

The preferred embodiments of the various steps a) to g) and of the treatment of the insect cuticles with an oxidizing agent are as stated above or in the corresponding step in the preferred embodiment below.

The invention also relates to a chitosan obtainable by a method according to the invention.

The chitin and/or chitosan obtainable by a method according to the invention can advantageously be used in various applications:
in cosmetic, pharmaceutical, nutraceutical or dietetic compositions,
as biomaterials for treating burns, as second skin, for making corneal dressings or suture materials,
as filtering, texturizing, flocculating and/or adsorbent agents in particular for water filtration and purification.

According to a preferred embodiment of the invention, the method comprises the following steps, described schematically in FIG. 1. It should be noted that certain steps are indicated as optional in this preferred embodiment.

Step 1: Killing the Insects

This killing step 1 makes it possible to kill the insects while reducing the microbial load (reducing the risk of deterioration and health risk) and by inactivating the internal enzymes of the insects which can trigger autolysis, and thus a rapid browning thereof.

Killing can be carried out by scalding.

The insects, preferably larvae, are thus scalded with water for 2 to 20 min, preferably 5 to 15 min. Preferably, the water is at a temperature comprised between 95 and 105° C., preferably 100° C.

The quantity of water introduced in this scalding step 1 is determined as follows: the ratio of the volume of water in mL to the weight of insect in g is preferably comprised between 0.3 and 10, more preferably between 0.5 and 5, even more preferably between 0.7 and 3, even more preferably of the order of 1.

Alternatively, killing can be carried out by blanching. Preferably, the insects are blanched with steam (steam nozzles or bed) at a temperature comprised between 80 and 130° C., preferably between 90 and 120° C., more preferably between 95 and 105° C., even more preferably 98° C. or with water at a temperature comprised between 95 and 105° C., preferably 100° C. (by spray nozzles) or in mixed mode (water+steam) at a temperature comprised between 80 and 130° C., preferably between 90 and 120° C., more preferably between 95 and 105° C. The residence time in the blanching chamber is comprised between 1 and 15 minutes, preferably between 3 and 7 min.

In this step, it is also possible to treat the insect cuticles using scalding or blanching water comprising the oxidizing agent according to the details indicated in the intermediate step below.

Intermediate Step (Optional): Treatment of Cuticles with the Oxidizing Agent

A special step of treatment of the cuticles with the oxidizing agent can be incorporated in the method. Advantageously, this intermediate step of treatment of the cuticles is carried out between the killing step 1 and the grinding step 2.

This intermediate step is preferably carried out with an oxidizing agent selected from the group constituted by hydrogen peroxide ($H_2O_2$), potassium permanganate ($KMnO_4$), ozone ($O_3$) and sodium hypochlorite (NaClO), more preferably hydrogen peroxide.

According to a first embodiment, at the end of step 1, when the latter is carried out by scalding, the oxidizing agent is introduced directly into the scalding tank, after optional cooling of the scalding water to a temperature of the order of 40 to 60° C., preferably of the order of 50° C.

The hydrogen peroxide as marketed is usually in the form of an aqueous solution, for example a solution at 30% by weight based on the total weight of water.

The quantity of hydrogen peroxide introduced for the treatment is such that the hydrogen peroxide content is comprised between 1 and 33% by weight based on the total weight of insects, preferably 2 to 12% by weight based on the total weight of insects, preferably of the order of 6% by weight.

According to a second embodiment, the insects are removed from the scalding tank, sieved and reintroduced into a tank.

The hydrogen peroxide is then introduced into the tank in the form of a dilute aqueous solution, the hydrogen peroxide content then being comprised between 1 and 33% by weight based on the weight of water, preferably 2 to 12% by weight based on the weight of water, and preferably of the order of 6% by weight.

Step 2: Grinding

The insects are removed from the scalding or treatment tank or from the blanching chamber, then they are sieved, and placed in a grinder, such as a knife mill, making it possible to reduce the insects to particles.

In order to facilitate the grinding, a quantity of water can be added. This quantity of water is similar to that introduced during the scalding step 1: the ratio of the volume of water in mL to the weight of insect in g is preferably comprised between 0.3 and 10, more preferably between 0.5 and 5, even more preferably between 0.7 and 3, even more preferably of the order of 1. It is also possible to keep the scalding water and/or the water resulting from the intermediate step in order to carry out this step. This water is likely to contain the oxidant. In this case, treatment of the cuticles can take place during the scalding step 1 and the grinding step 2 or during the intermediate step of treatment of the cuticles and during the grinding step.

Preferably, on completion of the grinding, the size of the insect particles is less than 1 cm (largest particle size observable using a microscope), preferably less than 0.5 cm.

Preferably, the size of the particle is comprised between 300 μm and 0.5 cm, more preferably between 500 μm and 0.5 cm, and even more preferably between 500 μm and 1 mm.

It is not necessary to excessively reduce the size of the particle, for example to a size less than 250 μm.

This grinding step 2 promotes access of the enzymes to their substrate.

In this step, it is possible to introduce the oxidizing agent into the grinding mill in order to treat the cuticles according to the methods indicated in the preceding intermediate step.

When treatment of the cuticles is not carried out concomitantly with grinding, during this step it is possible to add antioxidant additives that are commonly used for product preservation and stability.

Step 3: Pressing the Insect Cuticles

The wet paste originating from the grinding step 2 is then placed in a press according to a procedure which makes it possible to press and separate a juice comprising both a fat fraction and a protein fraction.

Preferably, the pressing step makes it possible to obtain a press cake comprising an oil content less than or equal to 20%, preferably less than or equal to 15%, more preferably less than or equal to 12%, even more preferably less than or equal to 10%.

Similarly, the pressing step makes it possible to obtain a press cake having a dry matter content comprised between 30% and 60%, preferably comprised between 40% and 55%, and more preferably comprised between 45% and 50%.

Any press system can be used for carrying out the pressing step, such as for example a single-screw or twin-screw press (twin-screw press of the Angel type), a filter-press (filter-press of the Choquenet type), a platen press, etc. These systems are well known to a person skilled in the art, who is able to determine the pressing conditions in order to obtain the oil and/or water contents mentioned above.

If the wet paste from the grinding step 2 was obtained with water comprising the oxidant, it can be advantageous to eliminate at least a part of this oxidant before the pressing step 3.

This pressing step 3 can optionally be carried out before the grinding step 2 starting from the scalded insects. However, it is advantageous to carry out the pressing step 3 after the grinding step 2.

This pressing step 3 therefore makes it possible to obtain a press juice and a press cake.

Step 4: Enzymatic Hydrolysis

The wet paste originating from the grinding step 2 or the press cake originating from the pressing step 3 is placed in a hydrolysis tank with water.

Optionally, and as will be described below, the protein fraction originating from the separating step 12 can be reintroduced in this enzymatic hydrolysis step 4, by mixing it with the press cake.

Optionally, and in the case when the scalding water does not contain oxidant, the scalding water can be recovered and reintroduced in the hydrolysis step. In fact, this water contains insect fractions that have been solubilized by the action of this scalding, and by using the latter in the hydrolysis it is possible to reduce the losses. Optionally, this water from scalding can be defatted, as certain waxes can have dissolved in the water.

The quantity of water introduced in this enzymatic hydrolysis step 4 is similar to that introduced in the scalding step 1: the ratio of the volume of water in mL to the weight of insect in g is preferably comprised between 0.3 and 10, more preferably between 0.5 and 5, even more preferably between 0.7 and 3, even more preferably of the order of 1.

Enzymatic hydrolysis is carried out with a protease, such as a commercial protease, for 4 to 8 h, more particularly for 4 to 5 h, at a pH from 6 to 8, more particularly from 6.5 to 7.5, at a temperature from 40 to 60° C., more particularly from 45 to 55° C.

The quantity of enzymes introduced in the hydrolysis step is less than 10% by weight based on the estimated total weight of dry matter entering hydrolysis, preferably less than 6%, more preferably of the order of 2%.

Proteolytic hydrolysis results in the production of a soluble phase containing the peptides, glucosamines and oligochitins and a solid residue formed from chitin, mainly chitin-polypeptide copolymer.

Step 5: Heat Inactivation

In order to stop the activity of the enzymes of the reaction and stabilize the soluble phase of the hydrolysis, heat inactivation is carried out by heating this juice between 80 and 105° C. for 10 to 25 min, preferably 15 to 20 minutes. According to one procedure, this heat inactivation step 5 is carried out according to the usual sterilization techniques of the agri-food industry. According to another procedure, enzyme inactivation is carried out by heating under IR or UV radiation, or by microwave heating.

Step 6: Pressing

The solid residue, predominantly composed of chitin, is recovered and then pressed in a press for maximum draining of this residue, in order to reinject this pressate into the soluble phase. The pressed residue thus formed consists essentially of chitin, mainly in the form of chitin-polypeptide copolymer.

Steps 7 and 8 (Optional): Washing and Drying

The solid residue is then washed, filtered, washed again and then dried by the conventional technologies known to a person skilled in the art.

Advantageously, the drying system is designed to protect the structure of the chitin-polypeptide copolymer: the hydrometry, ventilation and composition of the air are controlled. Advantageously, drying can be carried out in a ventilated stove at a temperature from 60 to 80° C., preferably of the order of 70° C.

Optionally, these steps can comprise a final delipidation step: the solid residue is treated with HCl in order to remove the last lipid residues, in particular the cuticular waxes.

The next steps 9 to 11 are for transforming the chitin to chitosan and therefore are only used when the desired product is chitosan.

Step 9 (Optional): Grinding

The dried solid residue, comprising predominantly chitin, is then ground, for example in a cutting (knife) mill.

The production of chitosan from chitin, by the deacetylation reaction, largely depends on the size of the chitin particles. Thus, very fine grinding of the dried solid residue before deacetylation makes it possible to increase the yields and the rate of the deacetylation reaction significantly, as shown in Table 1 below:

TABLE 1

Efficiency of deacetylation according to previous grinding of chitin

|  | Grinding 30 s | Grinding 45 s | Grinding 60 s | Grinding 120 s |
|---|---|---|---|---|
| 50% of the particles | <174 μm | <117 μm | <95 μm | <67 μm |
| 90% of the particles | <310 μm | <244 μm | <157 μm | <159 μm |
| DA* | 99% | 90% | 85% | 80% |

*Measurement of the Degree of Acetylation DA

The conditions of the deacetylation carried out in the test reported in Table 1 are as follows: reaction time 4 h, 100° C., NaOH in aqueous solution at 30 vol %, in a ratio of estimated chitin:NaOH solution equal to 1:20.

Consequently, the solid residue is preferably ground to a particle size less than 200 μm, more preferably less than 160 μm.

Step 10: Deacetylation

The solid residue, optionally ground in step 9, is then placed in a reactor, to which concentrated sodium hydroxide solution is added, for 4 to 24 h, and preferably 6 to 18 h. Sodium hydroxide in aqueous solution at a content ranging from 30% to 40% is added at a ratio of weight in g of ground chitin/volume in mL of sodium hydroxide in aqueous solution comprised between 1:50 and 1:10, preferably of the order of 1:20. The tank is then heated, the deacetylation temperature being between 80 and 150° C., preferably between 90 and 120° C. and more preferably at 100° C.

Chitosan is thus obtained in powder form.

The chitosan can then undergo any operation known to a person skilled in the art allowing it to be functionalized, in particular by adding radicals (carboxylation, hydroxylation, etc.).

Step 11 (Optional): Drying

The chitosan powder is then dried at between 30 and 80° C., preferably between 50 and 70° C. and preferably at approximately 60° C., in order to obtain a powder having a dry matter content greater than 85%, more particularly greater than 90%.

The next steps are for recovering a fat fraction and a protein fraction from the juice obtained in the pressing step 3 and therefore are only used when such recovery is desired.

Step 12: Separation

The press juice undergoes one or more separating steps, in order to separate the fat fraction (insect oils) from the protein fraction (insect haemolymph proteins). These steps can be carried out by any oil separation technology well known to a person skilled in the art, such as centrifugation, decanting, separation by reverse osmosis, ultrafiltration, supercritical $CO_2$, etc., or a combination of several of these technologies.

Separation of the fat fraction can be complex, in view of the presence of oils of very varied compositions in insects, and the fatty acids can have short chains (C2-05) as well as very long chains (for example, for waxes: >C25). Raising the temperature above the melting point of these oils (approximately 38° C.) during centrifugation makes it possible to solubilize this cream and facilitate separation of the fat fraction from the rest of the juice. The centrifugate then undergoes decanting according to a procedure (of the decanter or Tricanter type), for best possible separation of the oils and proteins.

These steps thus make it possible to obtain a fat fraction.

Once separated from the fat fraction, the protein fraction can be mixed with the press cake originating from the pressing step 3 just before the hydrolysis step 4. In fact, often more than 20% of the proteins are lost in the juice in the pressing step 3, hence the benefit of recovering this fraction and subjecting it to the hydrolysis step.

Step 13 (Optional): Concentration

According to one procedure, concentration is carried out by vacuum evaporation of the aqueous part. The concentrate has a dry extract greater than 10%, preferably greater than 20%. This operation facilitates drying, and additives commonly used for product preservation and stability can be added in this step.

Step 14 (Optional): Drying

The concentrate is finally dried by technologies that are known to a person skilled in the art, for example spraying/atomization ("spray-drying"), which makes it possible to obtain an extract, i.e. a dry powder of concentrate rich in peptides and glucosamines, the glucosamines in particular originating from the partial hydrolysis of chitin by $H_2O_2$ (essentially).

Figure 2:
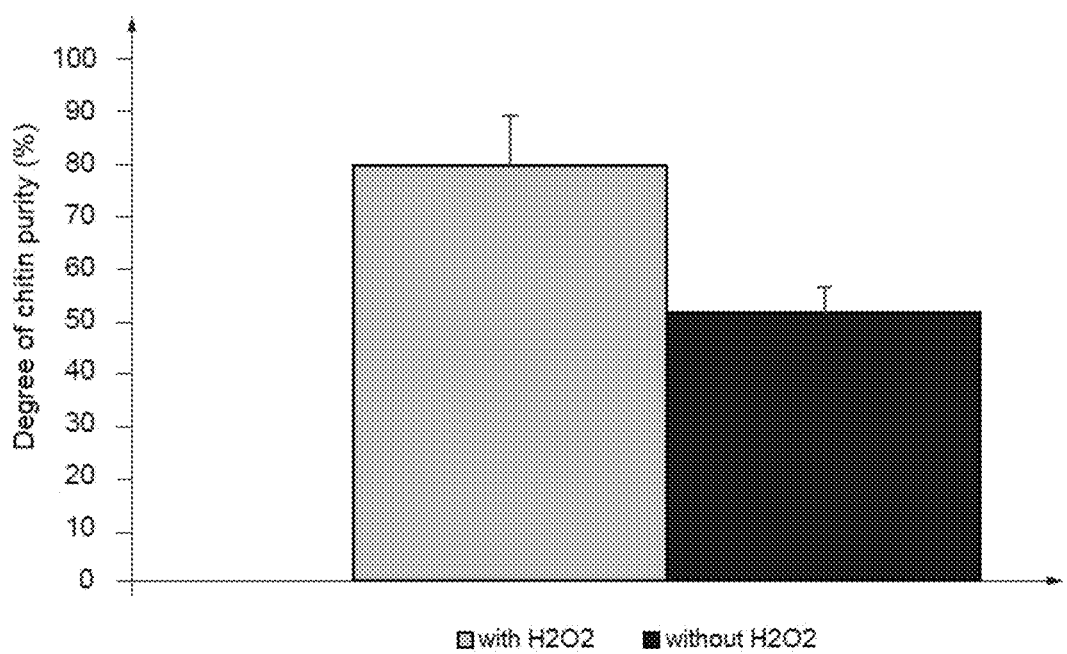
Figure 3:
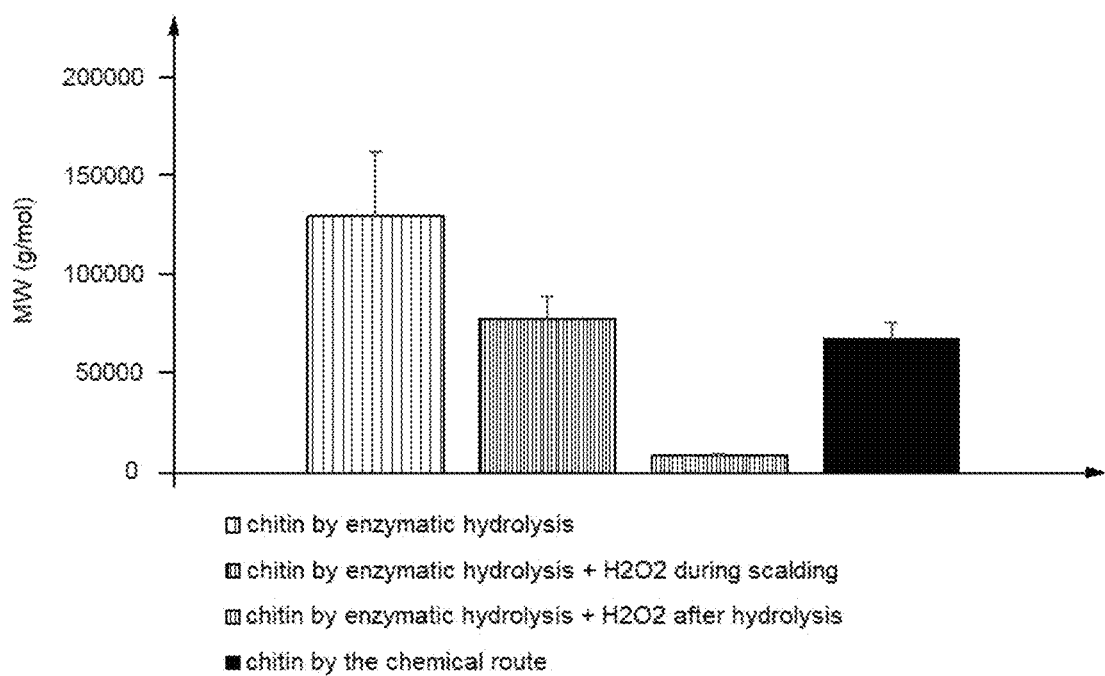
Figure 4:
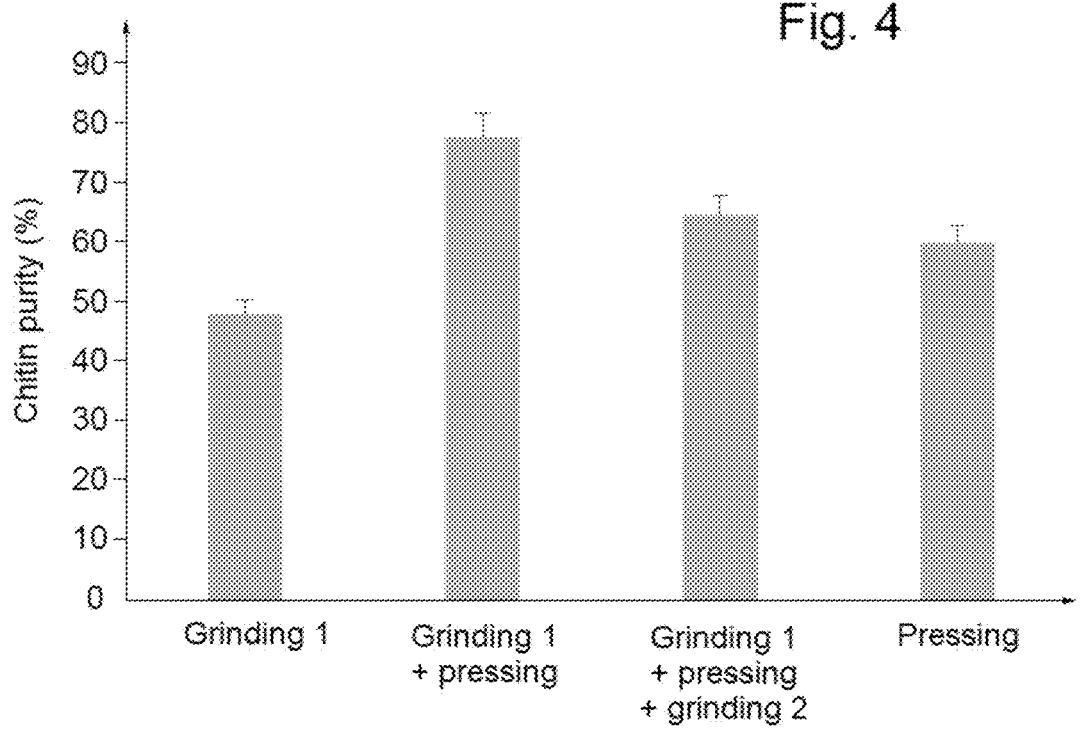
Figure 5:
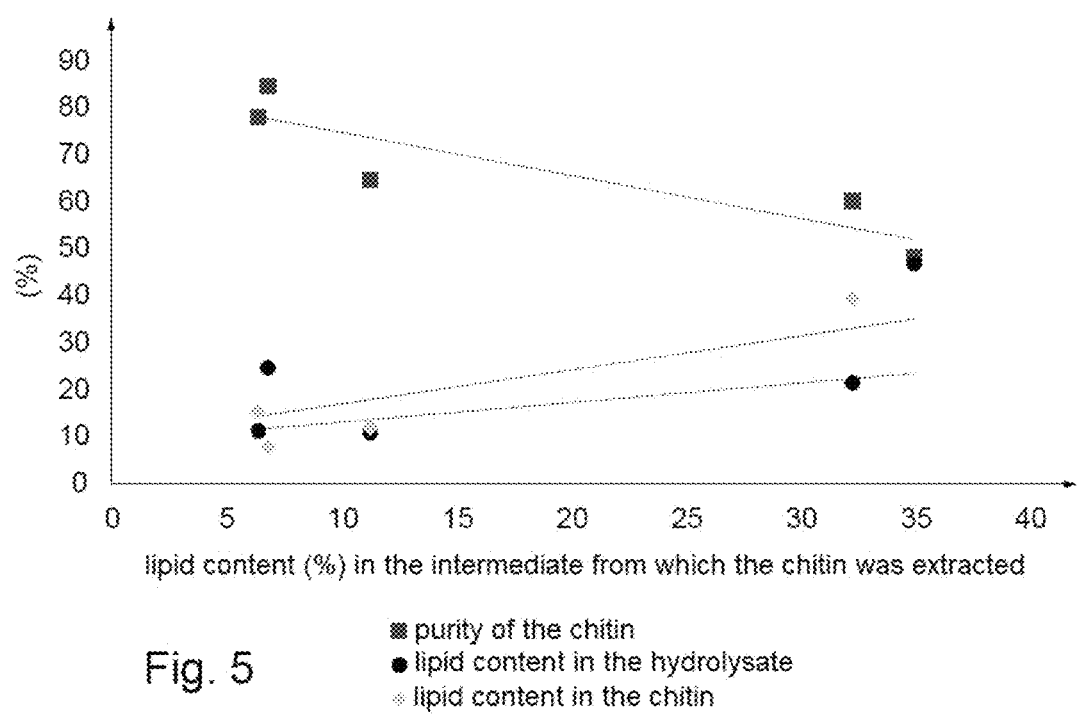
Figure 6:
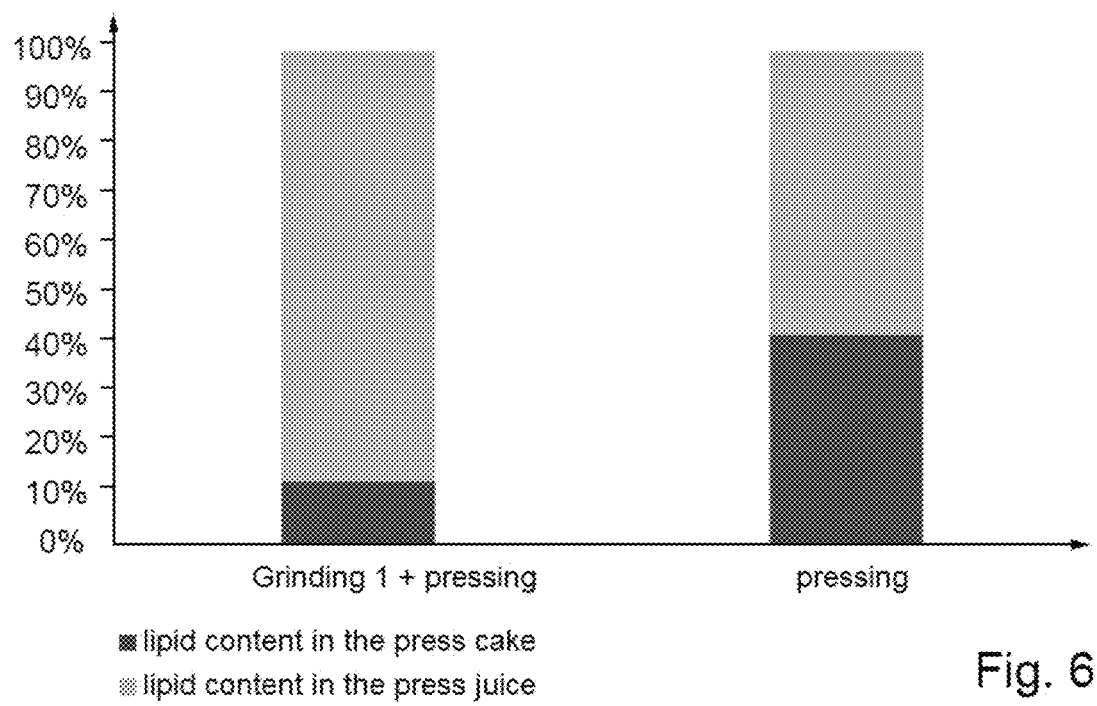
Figure 8:
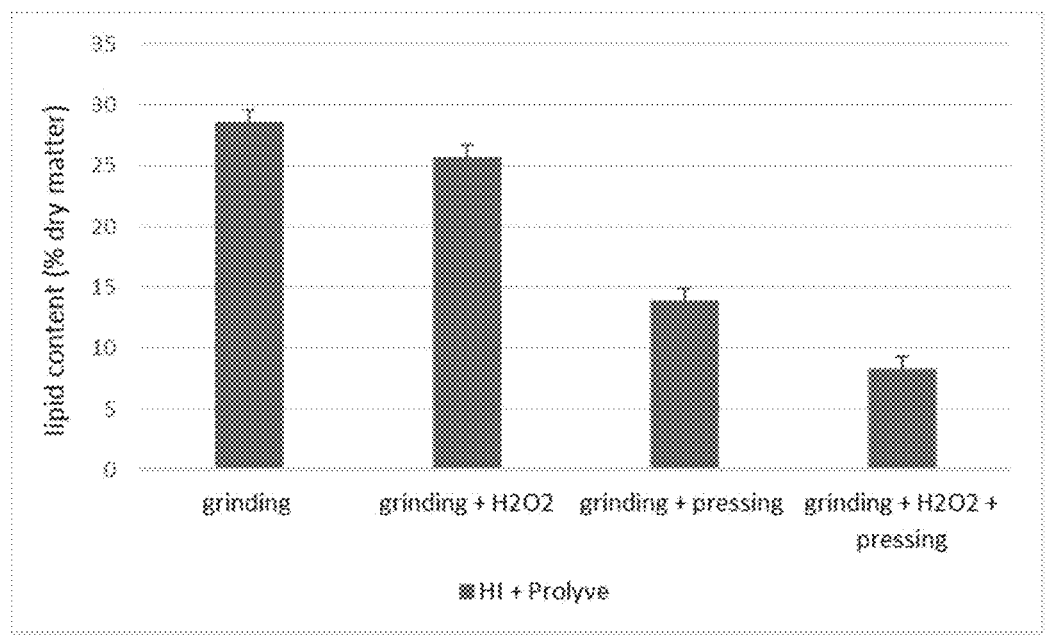
Figure 10:
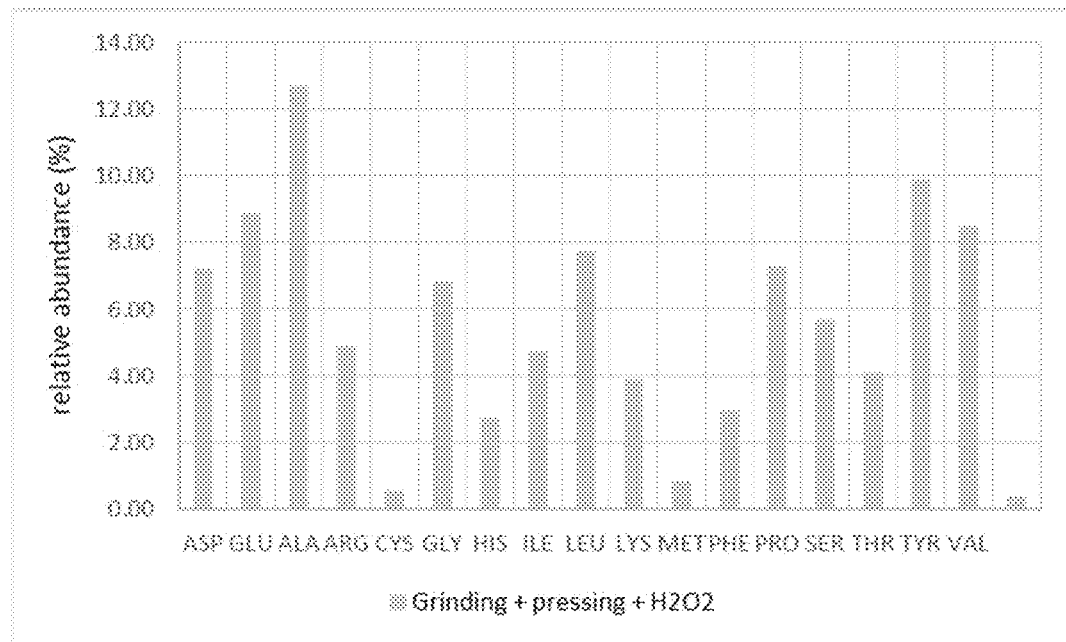
Figure 11:
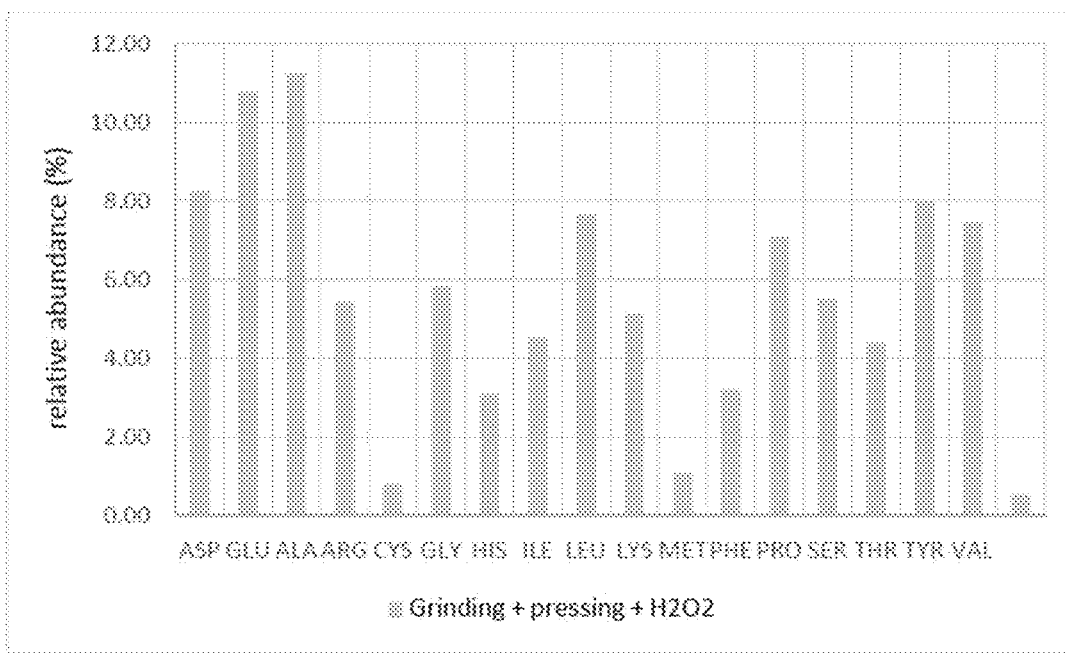
Figure 12:
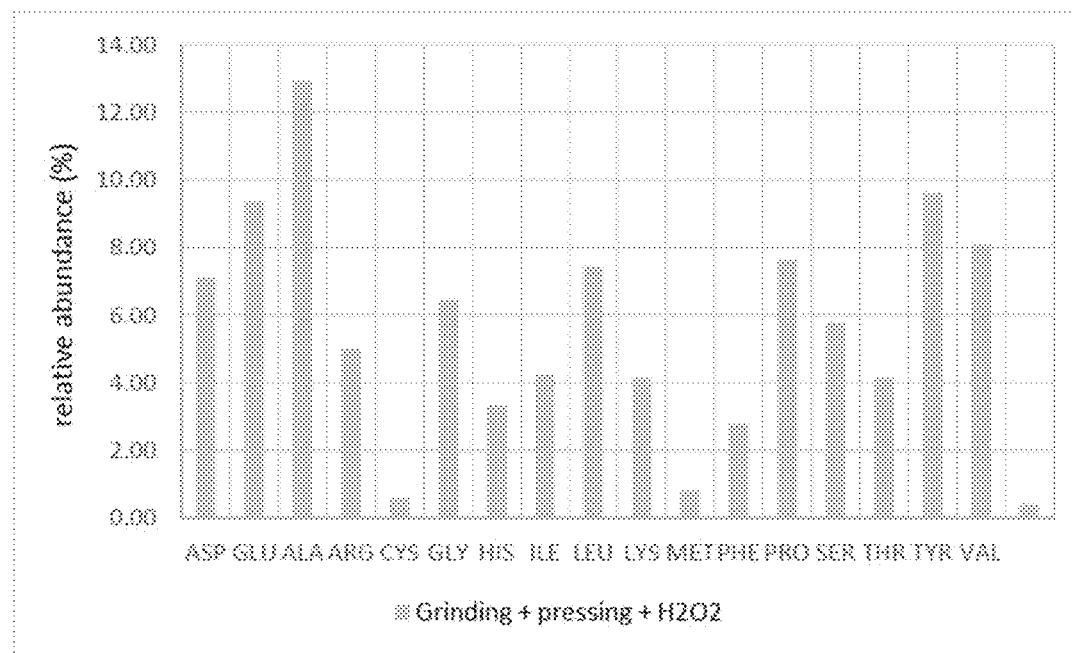
Figure 13:
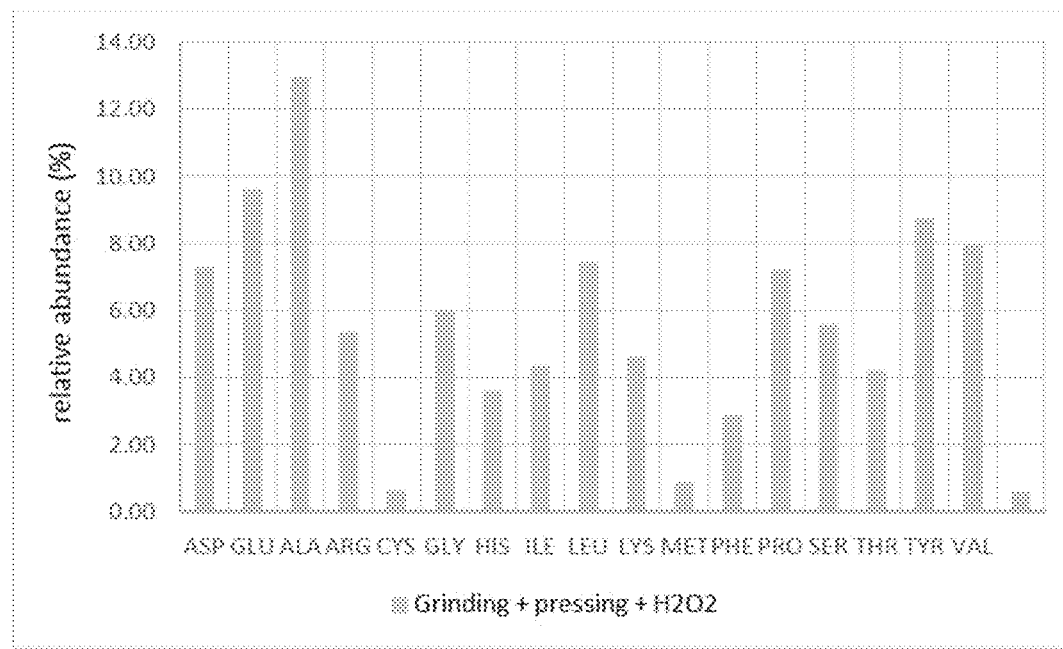
Figure 14:
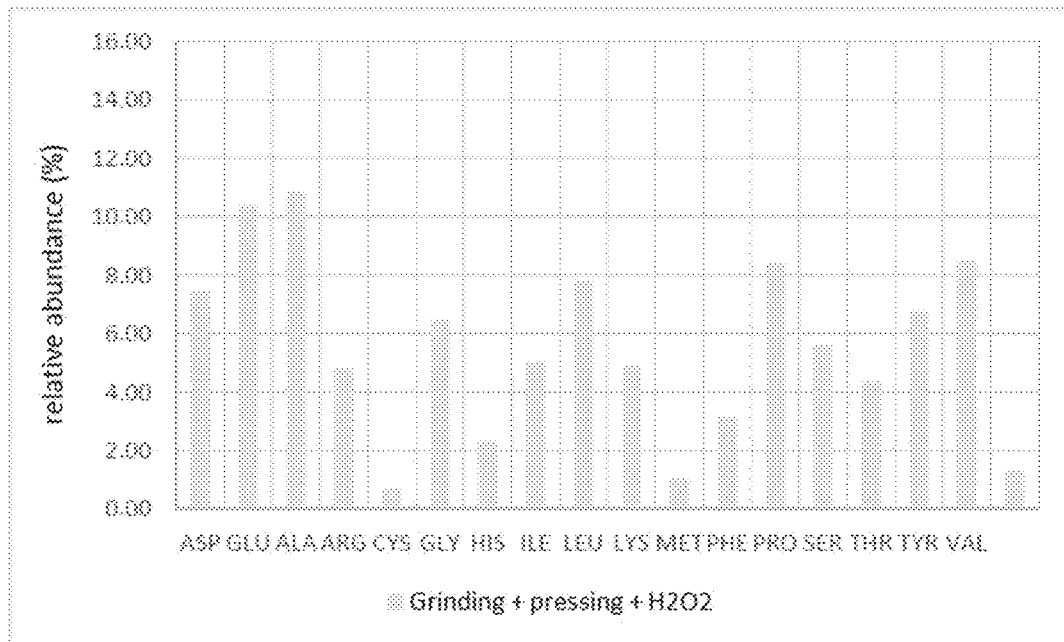
Figure 15:
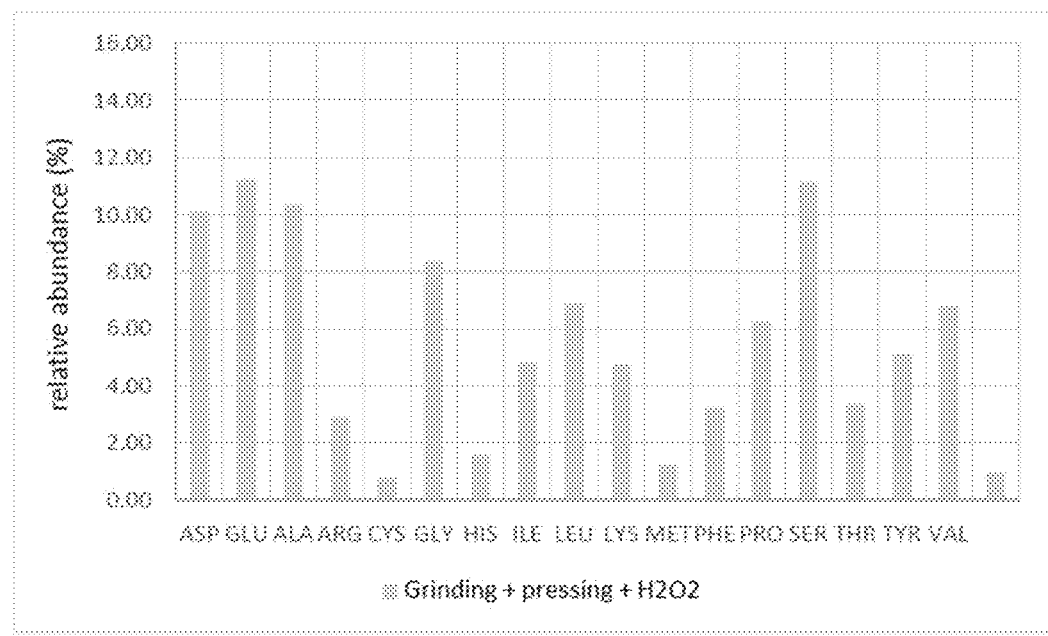
Figure 16:
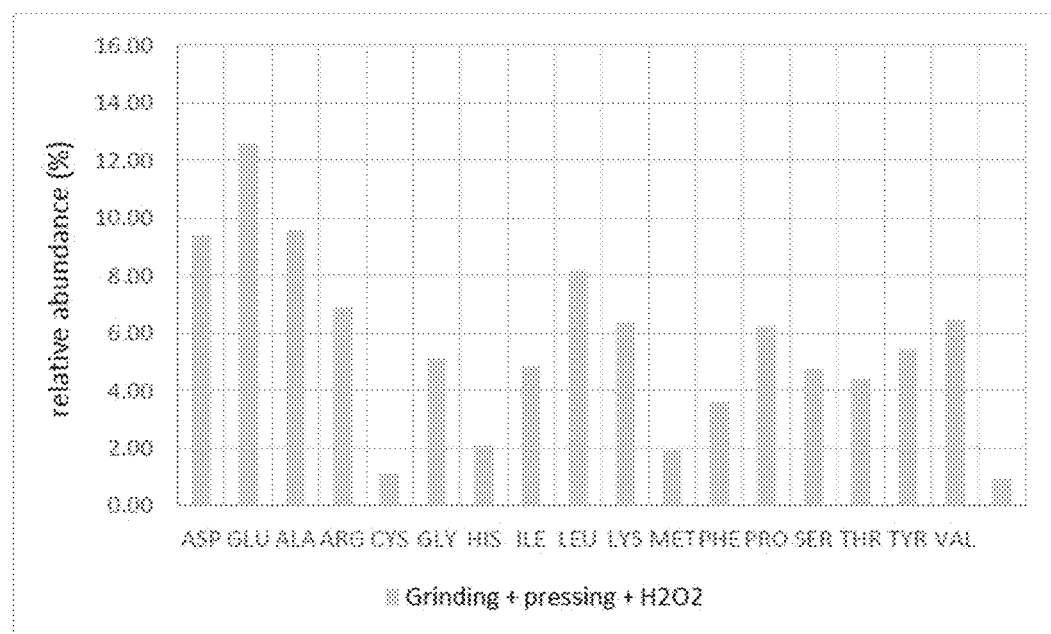
Figure 19:
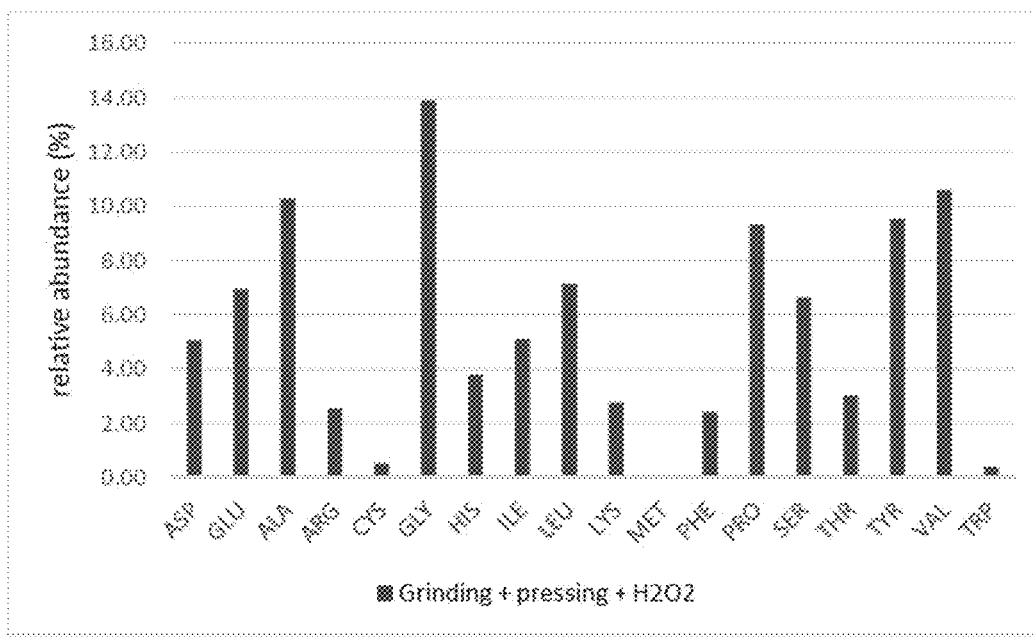
Figure 20:
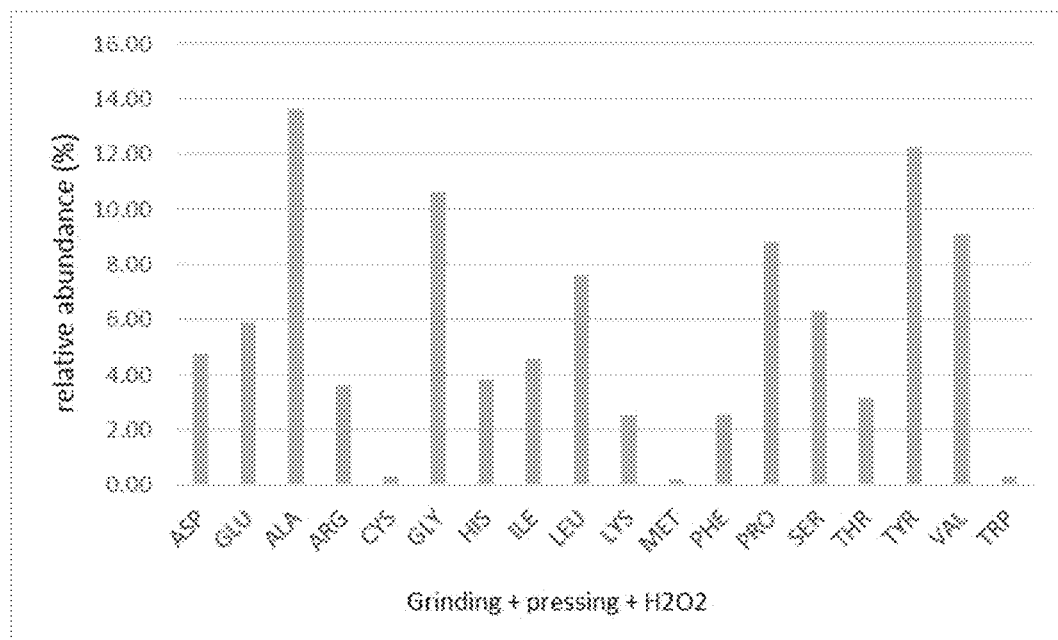
Figure 21:
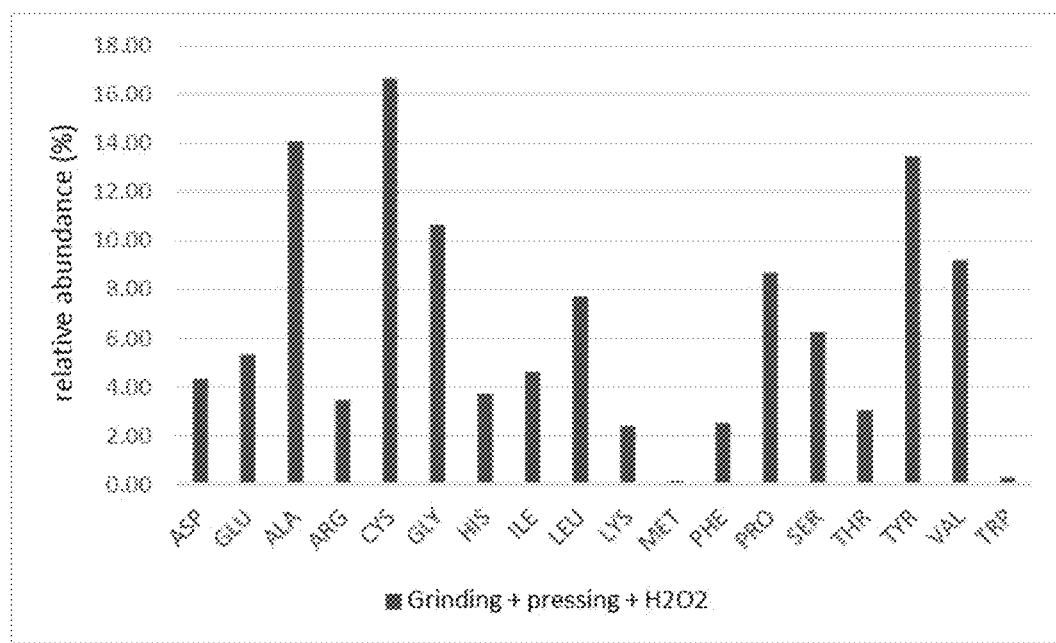
Figure 22:
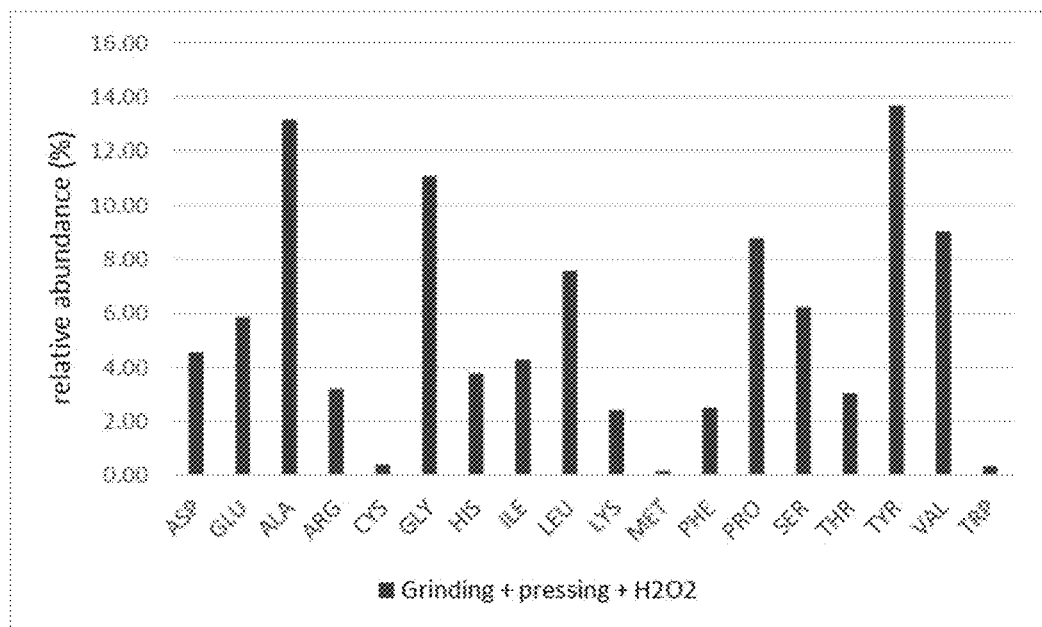
Figure 23:
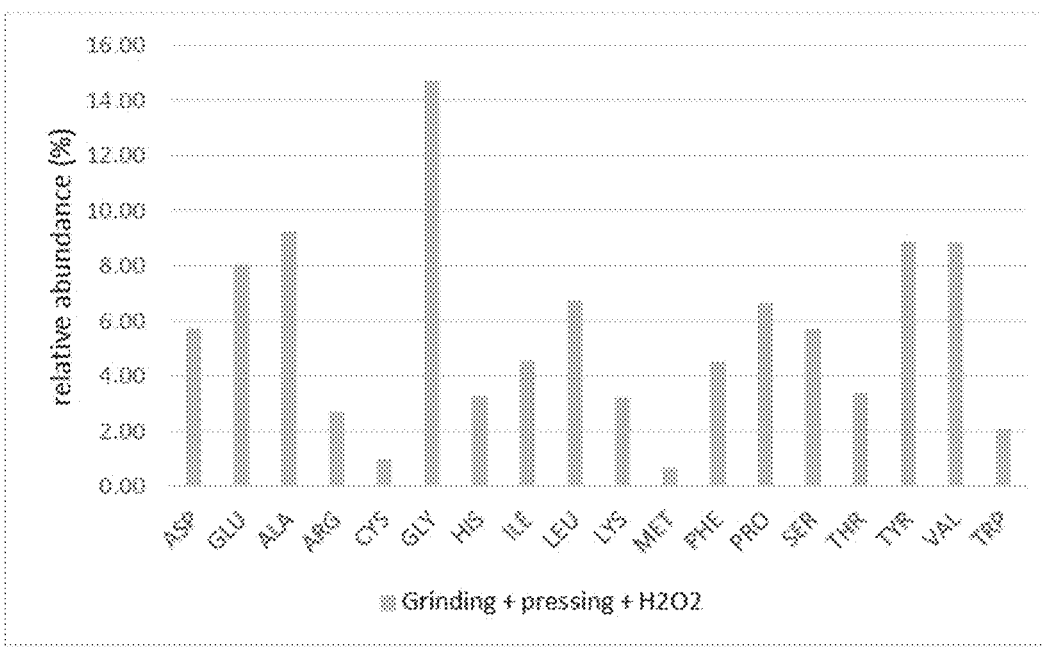
Figure 24:
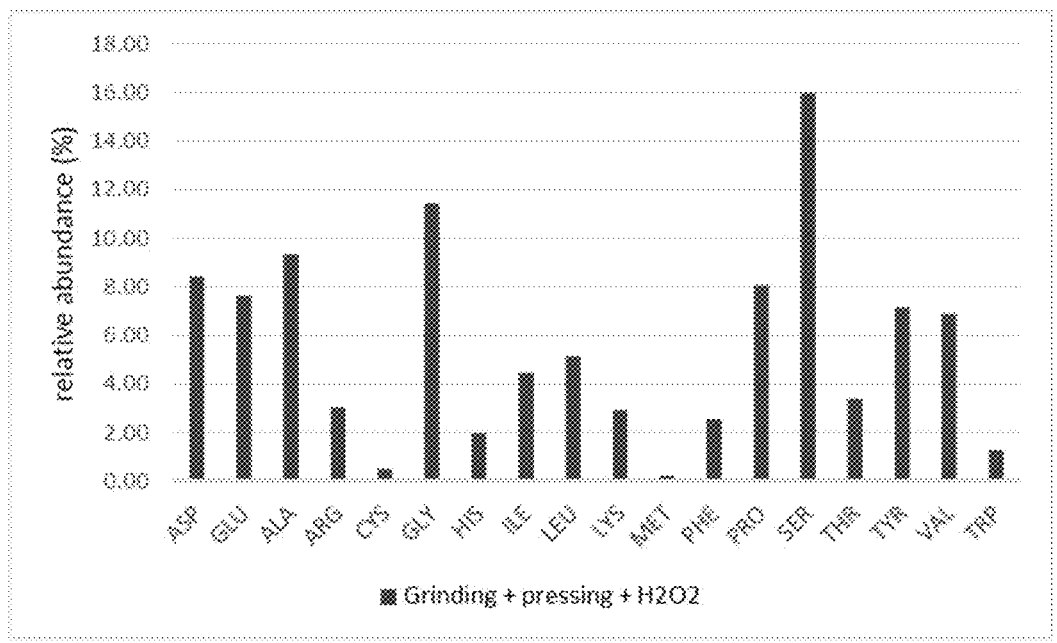
Figure 25:
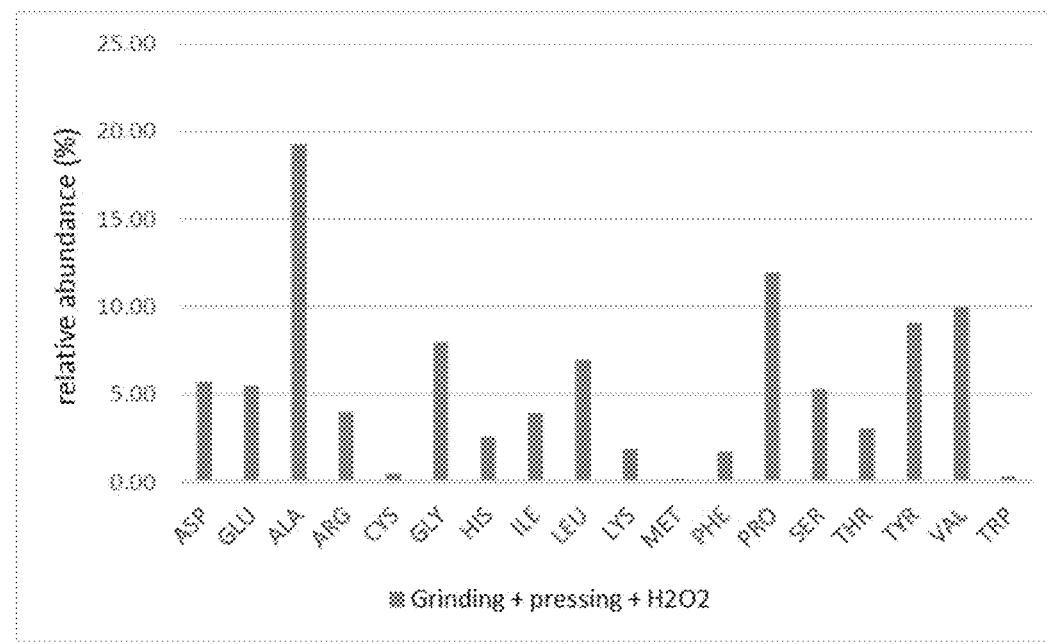

Other features and advantages of the invention will become clear from the following examples, given by way of illustration, with reference to the figures, which represent respectively:

FIG. 1 is a flow chart of a preferred embodiment of the method according to the invention, FIG. 2 is a diagram comparing the degree of purity of the chitin obtained by an enzymatic method with and without hydrogen peroxide, FIG. 3 is a diagram illustrating the influence of the method of extraction (enzymatic or chemical) and of the treatment with an oxidizing agent on the chitin obtained, FIG. 4 is a diagram comparing the degree of purity of the chitin obtained by an enzymatic method comprising one or more preliminary step(s) of grinding and pressing, FIG. 5 is a diagram comparing the lipid content measured in different fractions of intermediate product from which the chitin was extracted, FIG. 6 shows the distribution of the lipids between the press juice and the press cake obtained by an enzymatic method comprising steps prior to grinding and pressing or a step prior to pressing, FIG. 7 is a diagram comparing the degree of purity of the chitin obtained by an enzymatic method comprising one or more steps prior to the grinding operation(s), pressing and treatment with an oxidizing agent, FIG. 8: Effect of combining the steps on the lipid content in the hydrolysate, FIG. 9: Digestibility of the hydrolysate obtained by the method, FIG. 10: TM+Prolyve: relative abundance of amino acids in the hydrolysate, FIG. 11: TM+Sumizyme: relative abundance of amino acids in the hydrolysate, FIG. 12: TM+Novozyme: relative abundance of amino acids in the hydrolysate, FIG. 13: TM+Neutrase: relative abundance of amino acids in the hydrolysate, FIG. 14: HI+Prolyve: relative abundance of amino acids in the hydrolysate, FIG. 15: GM+Prolyve: relative abundance of amino acids in the hydrolysate, FIG. 16: AD+Prolyve: relative abundance of amino acids in the hydrolysate, FIG. 17: Effect of combining the oxidizing agent and the pressing step on the ash content in the chitin, FIG. 18: Synergy from combining the steps on the lipid content in the chitin, FIG. 19: TM+Prolyve: relative abundance of amino acids in chitin, FIG. 20: TM+Sumizyme: relative abundance of amino acids in chitin, FIG. 21: TM+Novozyme: relative abundance of amino acids in chitin, FIG. 22: TM+Neutrase: relative abundance of amino acids in chitin, FIG. 23: HI+Prolyve: relative abundance of amino acids in the hydrolysate, FIG. 24: GM+Prolyve: relative abundance of amino acids in the chitin, FIG. 25: AD+Prolyve: relative abundance of amino acids in the chitin, FIG. 26: Gravimetric purity of chitin—different enzymes, FIG. 27: Gravimetric purity of chitin—different insects, FIG. 28: Colorimetric purity of chitin obtained from *T. molitor*—different enzymes, FIG. 29: Colorimetric purity of chitin obtained by the method—different insects, FIG. 30: Purity by difference of the chitin obtained, and FIG. 31: Degree of crystallinity of the chitins obtained.

In the examples given below, any reference to a regulation or a directive concerns said regulation or said directive as in force on the filing date of the present application.

EXAMPLE 1: EXAMPLE OF A METHOD ACCORDING TO THE INVENTION 50 g of *T. molitor* larvae are introduced into a beaker, placed in a water bath at 100° C. containing 50 mL of 6% hydrogen peroxide solution, brought to the boil beforehand. After 5 minutes, the beaker is removed from the water bath, the larvae are drained, and then ground with a volume of water of 100 mL. The liquid thus obtained is passed into a press of the twin-screw type, which results in 17.89±0.87 g of press cake with a dry matter content of 20.9±1.3%, and 389.49±6.53 g of press juice with a dry matter content of 4.04±0.05%. 10 g (wet weight) of press cake thus obtained is transferred to an Erlenmeyer flask containing 50 mL of water and 0.1 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 µm. The chitin thus obtained is dried for 24 hours at 70° C. Thus, 0.64±0.05 g of chitin is obtained by this method.

EXAMPLE 2: INFLUENCE OF THE PRESENCE OF THE TREATMENT OF THE CUTICLES WITH THE OXIDANT ON THE DEGREE OF PURITY OF THE CHITIN OBTAINED 25 g of *T. molitor* larvae are introduced into a beaker, placed in a water bath at 100° C. containing 50 mL of water, brought to the boil beforehand. After 5 minutes, the beaker is removed from the water bath, the larvae are drained, and then ground with a volume of water of 25 mL. In the case of the reaction with hydrogen peroxide, the liquid thus obtained is placed in the presence of a solution of hydrogen peroxide for 1 hour, then transferred to a 250-mL Erlenmeyer flask containing a 4% protease solution (Sumizyme LP), otherwise it is transferred directly to the Erlenmeyer flask containing protease solution. The whole is placed under magnetic stirring for 4 hours at 45° C. (pH approximately 6.5). The Erlenmeyer flask is then placed for 15 minutes in a water bath at 90° C. in order to deactivate the enzymes, and the solution is then filtered hot at 0.45-0.5 µm. The chitin thus obtained is dried for 24 hours at 70° C.

The dry residue thus obtained after using hydrogen peroxide is 6.3±0.7% relative to the initial dry matter, whereas the dry residue resulting from a method without hydrogen peroxide is 9.75±0.9% relative to the initial dry matter.

The degree of purity of the chitin is determined compared to the weight of dry residue obtained relative to that resulting from chemical extraction, 5% of the initial dry matter. It is thus established at 79.9±9% for the product obtained after treatment with peroxide and at 51.5±4.9% in the absence of peroxide (see FIG. 2).

EXAMPLE 3: INFLUENCE OF THE ORDER OF THE SEQUENCE OF CARRYING OUT THE TREATMENT OF THE CUTICLES WITH THE OXIDANT AND ENZYMATIC HYDROLYSIS

Obtaining Chitin Enzymatically (without Adding Oxidant)

50 g of *T. molitor* larvae are introduced into a beaker, placed in a water bath at 100° C. containing 50 mL of water, brought to the boil beforehand. After 5 minutes, the beaker is removed from the water bath, the larvae are drained, and then ground with a volume of water of 100 mL. The liquid thus obtained is transferred to a 500-mL Erlenmeyer flask containing 150 mL of 1% protease solution (Prolyve), and the whole is placed under magnetic stirring for 4 hours at 45° C. (pH approximately 6.5). The Erlenmeyer flask is then placed for 15 minutes in a water bath at 90° C. in order to deactivate the enzymes, and the solution is then filtered hot at 0.45-0.5 µm. The chitin thus obtained is dried for 24 hours at 70° C. 1.656±0.021 g of chitin is obtained by this method.

Obtaining Chitin Enzymatically with the Addition of $H_2O_2$ During Scalding 50 g of *T. molitor* larvae are introduced into a beaker, placed in a water bath at 100° C. containing 50 mL of 6% $H_2O_2$ solution in water, brought to the boil beforehand. After 5 minutes, the beaker is removed from the water bath, the larvae are drained, and then mixed with a volume of water of 100 mL. The liquid thus obtained is transferred to a 500-mL Erlenmeyer flask containing 150 mL of 1% protease solution (Prolyve), and the whole is placed under magnetic stirring for 4 hours at 45° C. The Erlenmeyer flask is then placed for 15 minutes in a water bath at 90° C. in order to deactivate the enzymes, and the solution is then filtered hot at 0.45-0.5 µm. The chitin thus obtained is dried for 24 hours at 70° C. 1.98±0.22 g of chitin is obtained by this method.

Obtaining Chitin by the Enzymatic Route with the Addition of $H_2O_2$ after Hydrolysis 50 g of *T. molitor* larvae are introduced into a beaker, placed in a water bath at 100° C. containing 50 mL of water, brought to the boil beforehand. After 5 minutes, the beaker is removed from the water bath, the larvae are drained, and then ground with a volume of water of 100 mL. The liquid thus obtained is transferred to a 500-mL Erlenmeyer flask containing 150 mL of 1% protease solution (Prolyve), and the whole is placed under magnetic stirring for 4 hours at 45° C. (pH approximately 6.5). The Erlenmeyer flask is then placed for 15 minutes in a water bath at 90° C. in order to deactivate the enzymes, and the solution is then filtered hot at 0.45-0.5 µm. The residue is then placed in 6% $H_2O_2$ solution for 1 hour at 65° C. The chitin thus obtained is filtered (0.45-0.5 µm), and then dried for 24 hours at 70° C. 1.304±0.091 g of chitin is obtained by this method.

Obtaining Chitin by the Chemical Route 50 g of *T. molitor* larvae are introduced into a beaker, placed in a water bath at 100° C. containing 50 mL of water, brought to the boil beforehand. After 5 minutes, the beaker is removed from the water bath, the larvae are drained, and then ground with a volume of water of 60 mL. The liquid thus obtained is transferred with 50 mL of water to a 1 L bottle. 500 mL of 1M HCl is added and the whole is placed under stirring for 1 hour at 90° C. The reaction mixture is then filtered and washed with water until a clear residue is obtained. This residue is then transferred to a 1 L bottle, to which 500 mL of 1M NaOH is added and the whole is placed under stirring at 90° C. for 24 hours. The reaction mixture is then filtered and washed until a clear filtrate is obtained, and the residue is finally dried for 24 hours at 70° C. 0.944±0.005 g of chitin is obtained by this method.

Determination (by Viscometry) of the Molecular Weight of the Chitin Obtained

A flask containing 1 g of chitin and 10 mL of 1M NaOH is left to stand for 4 hours at 90° C. The mixture is then filtered (0.45-0.5 µm) and the residue thus washed is left to stand for 24 hours at 70° C.

Preparation of the solvent: 5 g of LiCl is placed in 100 mL of N,N-dimethylacetamide, and stirred for 4-5 hours (until completely dissolved).

The stock solution is obtained by dissolving 0.2 mg of chitin in 1 mL of solvent. Starting from this stock solution, dilutions are prepared, with concentrations of 0.1 mg/mL, 0.08 mg/mL and 0.04 mg/mL. The viscosity of these various solutions is then measured in triplicate with a viscometer of the Ostwald type and the molecular weight is calculated from the formula:

$$[\eta] = K M_w^\alpha \qquad (1)$$

with $[\eta]$: intrinsic viscosity in cm³/g,
$M_w$: molar mass of the chitin in g/mol (or Da), and
the Mark-Houwink coefficients α=0.71 and K=0.000893,
the intrinsic viscosity being obtained from:

$$[\eta] = \eta_r / C \qquad (2)$$

with $\eta_r$: reduced viscosity (without units),
C: concentration in mg/mL,
the reduced viscosity being obtained from:

$$\eta_r = t/t_0 \qquad (3)$$

with t: the falling time measured for the solution, in s,
$t_0$: the falling time measured for the solvent, in s.

It can be seen from FIG. 3 that the size of the molecule of the chitin obtained is a function of the extraction method used. Thus, the chemical method damages the integrity of the molecule ($M_w$ obtained is below 70,000 g/mol), but the harshest treatment is that which consists of bleaching the chitin with hydrogen peroxide after hydrolysis, even enzymatic hydrolysis ($M_w$ below 9,000 g/mol).

The method according to the invention (enzymatic hydrolysis with the addition of hydrogen peroxide during or just after scalding, i.e. at the beginning of the method), does reduce the size of the molecule relative to what can be found in the insect initially ($M_w$ of the chitin by simple enzymatic hydrolysis is 130,000 g/mol), but to a much smaller extent ($M_w$ close to 80,000 g/mol) and the result obtained is greater than that connected with conventional chemical extraction.

EXAMPLE 4: INFLUENCE OF THE PRESSING STEP PRIOR TO ENZYMATIC HYDROLYSIS ON THE DEGREE OF PURITY OF THE CHITIN OBTAINED

Different types of mechanical pretreatment were tested, grinding ("grinding 1") alone, grinding followed by pressing, grinding followed by pressing and a second grinding ("grinding 2"), as well as pressing alone.

For pressing, a press of the Angel type was used, under the following conditions:

Speed=82 rev/min;
W (energy)=3 HP (horsepower) or 2.68×10⁶ J;
Porosity (approximate)=0.5 mm in the first part and 0.2 mm in the last part.

1. Material and Methods

Production of Chitin with One Grinding 200 g of *T. molitor* larvae are introduced into a beaker, and placed in a water bath at 100° C. containing 200 mL of water brought to the boil beforehand. After 5 minutes, the beaker is removed from the water bath, the larvae are drained, and then mixed with a volume of water of 200 mL. The liquid thus obtained is transferred to a Erlenmeyer flask containing 2 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 8.13±0.27 g of chitin is obtained by this method.

Production of Chitin with Grinding Followed by Pressing 200 g of *T. molitor* larvae are introduced into a beaker, and placed in a water bath at 100° C. containing 200 mL of water brought to the boil beforehand. After 5 minutes, the beaker is removed from the water bath, the larvae are drained, and then mixed with a volume of water of 200 mL. The liquid thus obtained is passed into a press of the twin-screw type. 30 g of the press cake thus obtained is transferred to a Erlenmeyer flask containing 150 mL of water and 0.3 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 4.71±0.11 g of chitin is obtained by this method.

Production of Chitin with a First Grinding ("Grinding 1") Followed by Pressing and a Second Grinding ("Grinding 2")

200 g of *T. molitor* larvae are introduced into a beaker, and placed in a water bath at 100° C. containing 200 mL of water brought to the boil beforehand. After 5 minutes, the beaker is removed from the water bath, the larvae are drained, and then mixed with a volume of water of 200 mL. The liquid thus obtained is passed into a press of the twin-screw type. The press cake thus obtained is dried for 24 hours in an oven at 70° C., and then ground to 250 μm. 10 g of the powder thus obtained is transferred to a Erlenmeyer flask containing 50 mL of water and 0.1 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 4.93±0.12 g of chitin is obtained by this method.

Production of Chitin with Pressing Only 200 g of *T. molitor* larvae are introduced into a beaker, and placed in a water bath at 100° C. containing 200 mL of water brought to the boil beforehand. After 5 minutes, the beaker is removed from the water bath, the larvae are drained, and then passed into a press of the twin-screw type. 90 g of press cake thus obtained is transferred to a Erlenmeyer flask containing 450 mL of water and 0.9 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. Thus, 6.48±0.28 g of chitin is obtained by this method.

Production of Chitin by the Chemical Route 50 g of *T. molitor* larvae are introduced into a beaker, and placed in a water bath at 100° C. containing 50 mL of water, brought to the boil beforehand. After 5 minutes, the beaker is removed from the water bath, the larvae are drained, and then mixed with a volume of water of 60 mL. The liquid thus obtained is transferred to a 1-L vessel and 500 mL of 1M HCl solution is added. The whole is placed under stirring at 90° C. for 1 hour. The contents are then filtered and the solid residue is transferred to a 1-L bottle containing 500 mL of 1M NaOH solution; the whole is placed under stirring at 90° C. for 24 hours. The residue is then filtered and placed in a ventilated stove at 70° C. for 24 hours. Thus, 0.944±0.005 g of chemically purified chitin is obtained.

Calculation of the Degree of Purity

The degree of purity of the chitin is determined by comparing the weight of dry residue obtained relative to that resulting from chemical extraction, approximately 5% of the initial dry matter.

Measurement of the Lipid Content 2 g of sample is placed in a beaker, to which 0.2 g of $Na_2SO_4$ and 15 mL of $CHCl_3$/MeOH (2/1 v/v) are added. The whole is placed under magnetic stirring for 20 minutes, then the solution is filtered, and the residue is again placed in the beaker with 10 mL of $CHCl_3$/MeOH (2/1 v/v). The whole is placed under magnetic stirring for 15 minutes, then the solution is filtered, the solvent phases are combined and evaporated to constant weight. The lipid content is determined as a percentage by weight after extraction-evaporation relative to the initial weight of the sample (2 g).

2. Results

As can be seen from FIG. 4, the method has an influence on the purity of the chitin obtained, the best results being obtained with minimal pressing. The best result is obtained with grinding followed by pressing, namely a chitin having a degree of purity of 78% and the poorest with grinding alone, namely a chitin having a degree of purity of 48%.

Finer analysis of the intermediate from which the chitin was extracted shows that a low lipid content promotes greater purity of the chitin obtained (FIG. 5). By "intermediate" is meant the product entering enzymatic hydrolysis, i.e. originating from the last step before hydrolysis, namely according to the aforementioned methods of production, grinding step 1 or 2 or the pressing step.

Analysis of the lipid content in the chitin and the hydrolysis juice in fact shows that as a function of the initial lipid content present in the intermediate, the lipid content in the chitin is relatively stable, from 7 to 15%, whereas the lipid content in the hydrolysate varies from 11 to 47% (FIG. 3).

More particularly, if the intermediate has a lipid content of 35%, then:

the chitin that will result from hydrolysis will only be 50% pure and will comprise 10% lipids, and the lipid content of the hydrolysate will itself be close to 40%.

However, if the lipid content of the intermediate is 7%, then:

the chitin obtained after hydrolysis will have a purity of 80% and will have a lipid content of 8% and the hydrolysate will also have a low lipid content, of the order of 10%.

This indicates that when the initial lipid content is high, greater than 12%, the enzyme responsible for hydrolysis is caused to hydrolyse not only the proteins, but also the lipids by catalytic promiscuity. Thus, a similar lipid content in the chitin is obtained, namely 8.6 and 7.9%, in cases when the initial lipids were 35 and 7% respectively. However, the purity of the chitin passes in this case from 48 to 84% respectively. Thus, of the 52% of impurities on the one hand and 16% on the other hand, 8% on average are due to the lipids, and the quantity of proteins still attached to the chitin is therefore 38 points higher in the case when more lipids were present in the intermediate subjected to hydrolysis.

Finally, the importance of grinding upstream of pressing can also be studied (FIG. 6). Thus, it can clearly be seen that the distribution of the lipids between the cake and the press juice is far more effective, 12.9 versus 87.1, against 42.7 versus 57.3 when a preliminary grinding was carried out.

EXAMPLE 5: INFLUENCE OF THE COMBINATION OF STEPS PRIOR TO ENZYMATIC HYDROLYSIS ON THE DEGREE OF PURITY OF THE CHITIN OBTAINED

Different types of pretreatment were tested, grinding alone, grinding followed by pressing, treatment of the cuticles with an oxidizing agent ($H_2O_2$) followed by grinding and treatment of the cuticles with an oxidizing agent ($H_2O_2$) followed by grinding and pressing.

For pressing, the press of the Angel type described in Example 4 was used, under the following conditions:
Speed=82 rev/min;
W (energy)=3 HP (horsepower) or $2.68 \times 10^6$ J;
Porosity (approximate)=0.5 mm in the first part and 0.2 mm in the last part.

1. Material and Methods

Production of Chitin with Grinding 200 g of *T. molitor* larvae are introduced into a beaker, placed in a water bath at 100° C. containing 200 mL of water, brought to the boil beforehand. After 5 minutes, the beaker is removed from the water bath, the larvae are drained, and then mixed with a volume of water of 200 mL. The liquid thus obtained is transferred to an Erlenmeyer flask containing 2 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. 8.13±0.27 g of chitin is obtained by this method.

Production of Chitin with Grinding Followed by Pressing 200 g of *T. molitor* larvae are introduced into a beaker, placed in a water bath at 100° C. containing 200 mL of water, brought to the boil beforehand. After 5 minutes, the beaker is removed from the water bath, the larvae are drained, and then ground with a volume of water of 200 mL. The liquid thus obtained is passed through a press of the twin-screw type. 30 g of the press cake thus obtained is transferred to an Erlenmeyer flask containing 150 mL of water and 0.3 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. 4.71±0.11 g of chitin is obtained by this method.

Production of Chitin with Treatment of the Cuticles with an Oxidizing Agent ($H_2O_2$) Followed by Grinding 50 g of *T. molitor* larvae are introduced into a beaker, placed in a water bath at 100° C. containing 50 mL of 6% hydrogen peroxide solution, brought to the boil beforehand. After 5 minutes, the beaker is removed from the water bath, the larvae are drained, and then ground with a volume of water of 100 mL. The liquid thus obtained is transferred to an Erlenmeyer flask containing 150 mL of water and 0.5 g of protease (Prolyve), and the whole is placed under magnetic stirring for 4 hours at 45° C. (at a pH of approximately 6.5). The Erlenmeyer flask is then placed for 15 minutes in a water bath at 90° C. in order to deactivate the enzymes, and the solution is then filtered hot at 0.45-0.5 μm. The chitin thus obtained is dried for 24 hours at 70° C. 1.98±0.22 g of chitin is obtained by this method.

Production of Chitin with Treatment of the Cuticles with an Oxidizing Agent ($H_2O_2$) Followed by Grinding and Pressing This test is carried out according to Example 1.

Calculation of the Degree of Purity

The chitin purity is calculated by gravimetry as a function of the chitin content initially contained in the larvae, i.e. approximately 5% of the dry weight of the larvae.

2. Results

The results are presented in FIG. 7. The purity of the chitin obtained by enzymatic hydrolysis is highly dependent on the pretreatment method used. Thus, when only grinding is carried out before enzymatic hydrolysis, this method only results in a purity of 48%, whereas the addition of a pressing step or of treatment of the cuticles with an oxidizing agent makes it possible to obtain a purity of 50-78%. Finally, combining a pressing step with treatment of the cuticles with an oxidizing agent makes it possible to obtain a chitin having a degree of purity of 88%.

Synergy Effect Resulting from Combining a Pressing Step with a Step of Treating the Cuticles with an Oxidizing Agent Table 2 below summarizes the results presented in FIG. 7.

TABLE 2

Improvement in the purity of the chitin depending on the pretreatment method used

|  | Grinding alone | Grinding + pressing | $H_2O_2$ + Grinding | $H_2O_2$ + grinding + pressing |
|---|---|---|---|---|
| Purity of the chitin obtained | 48% | 78% | 50% | 88% |
| Improvement in the purity of the chitin relative to grinding alone | — | +63% | +4% | +83% |

Table 2 demonstrates the synergistic effect of combining a pressing step and a step of treatment with an oxidizing agent.

EXAMPLE 6: CHARACTERIZATION OF THE HYDROLYSATE AND THE CHITIN ACCORDING TO THE PRODUCTION METHOD USED

I. Material and Methods a) Material

Insects

Various insects were studied:
a coleopteron: *Tenebrio molitor* (*T. molitor* or TM),
a lepidopteron: *Galleria mellonella* (*G. mellonella* or GM),
a dipteron: *Hermetia illucens* (*H. illucens* or HI), and
an orthopteron: *Acheta domesticus* (*A. domesticus* or AD).

Enzymes

Various enzymes were used in the hydrolysis step.

This measurement of the enzymatic activity is based on the principle of measurement of tyrosine release at 275 nm during hydrolysis of casein by a proteolytic enzyme (Valley Research SAPU Assay method, by Karen PRATT).

$$\frac{SAPU}{g} = \frac{(\Delta A - i) \times 11}{m \times 30 \times C \times 1}$$

SAPU/g=one spectrophotometric unit of protease
ΔA=correlated absorbance
i=y-axis at origin
11=final reaction volume
M=slope of the calibration curve
30=reaction time (in minutes)
C=concentration of the enzyme (g/mL) in the enzyme solution added
1=1 mL volume of the enzyme solution added The calibration curve is obtained by measuring the absorbance of tyrosine solutions of different concentrations in a phosphate buffer (0.2 M, pH 7).

5 mL of a solution of casein (0.7% w/v, phosphate buffer 0.2 M, pH 7, heated for 30 minutes at 90° C. and with 3.75 g/L$_{solution}$ added) is incubated with 1 mL of the enzyme solution (0.15 g in 100 mL of glycine buffer, 0.05M) to be tested at 37° C. for 30 minutes. Then 5 mL of TCA solution is added (18 g TCA, 11.35 g of anhydrous sodium acetate, 21 mL of glacial acetic acid, made up with demineralized water to 1 litre of solution), mix on a vortex, filter and measure the absorbance at 275 nm.

The control is prepared identically but without adding enzyme, 1 mL of demineralized water is added instead in order to have the same reaction volume.

The activities thus measured for the various enzymes used (Prolyve NP, Novozyme 37071, Neutrase and Sumizyme) are listed in Table 3.

TABLE 3

Correspondence of the activities and enzyme masses of the enzyme used

| | enzyme | | | |
|---|---|---|---|---|
| | Prolyve | Novozyme | Neutrase | Sumizyme |
| Desired enzymatic activity | 3789.52 | 3789.52 | 3789.52 | 3789.52 |
| Enzymatic activity/g | 3789.52 | 1662.35 | 2213.24 | 3237.19 |
| m (g) | 1.00 | 2.28 | 1.71 | 1.17 | b) Methods of Production

Method of Production with Grinding Only (Denoted "Grinding" in the FIGS.

600 g of fresh insects (either larvae in the case of *T. molitor, G. melonella* or *H. illucens*; or crickets in the case of *A. domesticus*) are introduced into a chamber, where they are killed with steam (115° C., 5 minutes). The insects are then introduced into a mixer and 75 mL of water is added per 100 g of insects, and the whole is then mixed. 100 g (wet weight) of product thus obtained is then introduced into a three-necked flask equipped with a condenser and a mechanical stirrer, and a proteolytic enzyme with an activity equivalent to 3789 SAPU is then added. The reaction mixture is then heated to 45° C. for 4 hours. The temperature is then raised to 90° C. for 15 minutes, and the reaction mixture is finally filtered (0.40-0.45 μm). The residue is dried for 24 hours at 70° C.: this is therefore chitin obtained by the enzymatic route of purification; the filtrate is frozen and lyophilized: this is the hydrolysate.

The method is identical whatever the insect or enzyme studied.

Method of Production with Grinding Followed by Pressing (Denoted "Grinding+Pressing" in the Figures)

600 g of fresh insects (either larvae in the case of *T. molitor, G. melonella* or *H. illucens*, or crickets in the case of *A. domesticus*) are introduced into a chamber, where they are killed with steam (115° C., 5 minutes). The insects are then introduced into a mixer and 75 mL of water is added per 100 g of insects, and the whole is then mixed and pressed (twin-screw press, or filter press, or other pressing system). 100 g (wet weight) of product thus obtained is then introduced into a three-necked flask equipped with a condenser and a magnetic stirrer, 500 mL of water is added, as well as a proteolytic enzyme with an activity equivalent to 3789 SAPU. The reaction mixture is then heated at 45° C. for 4 hours. The temperature is then raised to 90° C. for 15 minutes, and the reaction mixture is finally filtered (0.40-0.45 μm). The residue is dried for 24 hours at 70° C.: this is therefore chitin obtained by the enzymatic route of purification; the filtrate is frozen and lyophilized: this is therefore the hydrolysate.

The method is identical whatever the insect or enzyme studied.

Method of Production with Grinding and Oxidizing Treatment of the Insect Cuticles (Denoted "Grinding+H$_2$O$_2$" in the Figures)

600 g of fresh insects (either larvae in the case of *T. molitor, G. melonella* or *H. illucens*, or crickets in the case of *A. domesticus*) are introduced into a chamber, where they are killed with the vapour of a water/H$_2$O$_2$ mixture (6%) (115° C., 5 minutes). The insects are then introduced into a mixer and 75 mL of water is added per 100 g of insects, and the whole is then mixed. 100 g (wet weight) of the product thus obtained is then introduced into a three-necked flask equipped with a condenser and a mechanical stirrer, and a proteolytic enzyme with an activity equivalent to 3789 SAPU is then added. The reaction mixture is then heated at 45° C. for 4 hours. The temperature is then raised to 90° C. for 15 minutes, and the reaction mixture is finally filtered (0.40-0.45 μm). The residue is dried for 24 hours at 70° C.: it is therefore chitin obtained by the enzymatic route of purification; the filtrate is frozen and lyophilized: this is therefore the hydrolysate.

The method is identical whatever the insect or enzyme studied.

Method of Production with Grinding, Oxidizing Treatment of the Insect Cuticles and Pressing (Denoted "Grinding+H$_2$O$_2$+Pressing" in the Figures)

600 g of fresh insects (either larvae in the case of *T. molitor, G. melonella* or *H. illucens*, or crickets in the case of *A. domesticus*) are introduced into a chamber, where they are killed with the vapour of a water/H$_2$O$_2$ mixture (115° C., 5 minutes). The insects are then put in a mixer and 75 mL of water is added per 100 g of insects, and the whole is then mixed and pressed (twin-screw press, or filter press, or other pressing system). 100 g (wet weight) of the product thus obtained is then introduced into a three-necked flask equipped with a condenser and a magnetic stirrer, 500 mL of water is added as well as a proteolytic enzyme with an activity equivalent to 3789 SAPU. The reaction mixture is then heated at 45° C. for 4 hours. The temperature is then raised to 90° C. for 15 minutes, and the reaction mixture is finally filtered (0.40-0.45 μm). The residue is dried for 24 hours at 70° C.: this is therefore chitin obtained by the enzymatic route of purification; the filtrate is frozen and lyophilized: this is therefore the hydrolysate.

The method is identical whatever the insect or enzyme studied.

c) Analyses

Measurement of the Ash Content

The ash content was determined by the method based on EC Regulation 152/2009 dated 27 Jan. 2009.

Measurement of the Protein Content

The protein content is obtained by the Dumas method, with a conversion factor of 6.25, adapted from standard NF EN ISO 16634-1.

Measurement of the Lipid Content

The lipid content is obtained by a method adapted from EC Regulation 152/2009—method B—SN.

Pepsin Digestibility

Pepsin digestibility is measured by the method described in Directive 72/199/EC.

Relative Abundance of Amino Acids

The abundance of the amino acids was determined by a method derived from EC Regulation 152/2009 dated 27 Jan. 2009—SN. The tryptophan content was determined separately by a method adapted from EC Regulation 152/2009 dated 27 Jan. 2009—SN. The relative abundance was calculated by relating the content of each amino acid to the amino acid content.

Amino Acid Content

The amino acid content was determined by adding together the individual values obtained for each amino acid, including tryptophan.

Gravimetric Purity

Gravimetric purity is determined by comparing the weight of dry residue obtained relative to that resulting from chemical extraction, the latter being evaluated at approximately 5% of the initial dry matter.

Colorimetric Purity

The colour of the sample was estimated by analysing photographs of samples using the ImageJ software according to the three colours red, green and blue (RGB), their average representing an assessment of the true colour. A sample of prawn chitin marketed by Chitine France was taken as the standard (100% purity) and the colorimetric purity of the samples produced was calculated as a percentage of this colour (ratio of the colour of the sample to the colour of the standard).

Purity by Difference

For this measurement, the quantities of known impurities (amino acids, lipids and ash) were subtracted from the value of absolute purity (100%) to obtain the value of the purity estimated by difference; i.e. a sample that contains 30% proteins, 10% lipids and 1% ash is therefore assigned a purity of 100−30−10−1=59%.

Degree of Crystallinity

The measurements were carried out according to the WAXS (wide angle X-ray scattering) technique on Bruker D8 Advance apparatus (A25 DaVinci design) equipped with a Lynxeye XE detector. The results were interpreted following the method described in Loelovich, M. Res. Rev.: J. Chem. 2014, 3, 7-14.

II. Hydrolysate a) Ash

The ash content of the hydrolysate originating from the method "grinding+$H_2O_2$+pressing" was investigated on various insects and different enzymes. These ash contents, stated in % by weight of the hydrolysate, are shown in Table 4 below.

TABLE 4

Ash contents of the hydrolysate - different insects and enzymes

| | |
|---|---|
| TM + Prolyve | 2.3 |
| TM + Sumizyme | 2.5 |
| TM + Novozyme | 1.95 |
| TM + Neutrase | 2.6 |

TABLE 4-continued

Ash contents of the hydrolysate - different insects and enzymes

| | |
|---|---|
| HI + Prolyve | 3.3 |
| GM + Prolyve | 2.4 |
| AD + Prolyve | 2.4 |

Thus, for all the insects and enzymes tested, the ash content in the hydrolysate is <3.5%, and even for the insects having a low to moderate ash content naturally, this content is <3%.

b) Protein Content

The protein content in the hydrolysate originating from the method "grinding+$H_2O_2$+pressing" was investigated on various insects and different enzymes. These contents, stated in % by weight of the hydrolysate, are shown in Table 5 below.

TABLE 5

Protein content in the hydrolysate - different insects and enzymes

| | |
|---|---|
| TM + Prolyve | 81.2 |
| TM + Sumizyme | 80 |
| TM + Novozyme | 83.25 |
| TM + Neutrase | 85.1 |
| HI + Prolyve | 74.85 |
| GM + Prolyve | 76.6 |
| AD + Prolyve | 82.8 |

For all the insects and enzymes tested, the protein content in the hydrolysate is >74%, and even for the non-flying insects the content is ≥80%.

c) Lipid Content

The lipid content in the hydrolysate originating from the method "grinding+$H_2O_2$+pressing" was investigated on various insects and different enzymes. These contents, stated in % by weight of the hydrolysate, are shown in Table 6 below.

TABLE 6

Lipid content in the hydrolysate - different insects and enzymes

| | |
|---|---|
| TM + Prolyve | 2.9 |
| TM + Sumizyme | 4.4 |
| TM + Neutrase | 2.7 |
| HI + Prolyve | 8.3 |
| GM + Prolyve | 9.5 |
| AD + Prolyve | 3 |

Combining the step with the oxidizing agent and the pressing step helps to lower the lipid content in the hydrolysate significantly (FIG. 8). Thus, this content is less than 10% for all of the insects and even less than 5% for the non-flying insects.

d) Digestibility

Figure 9:
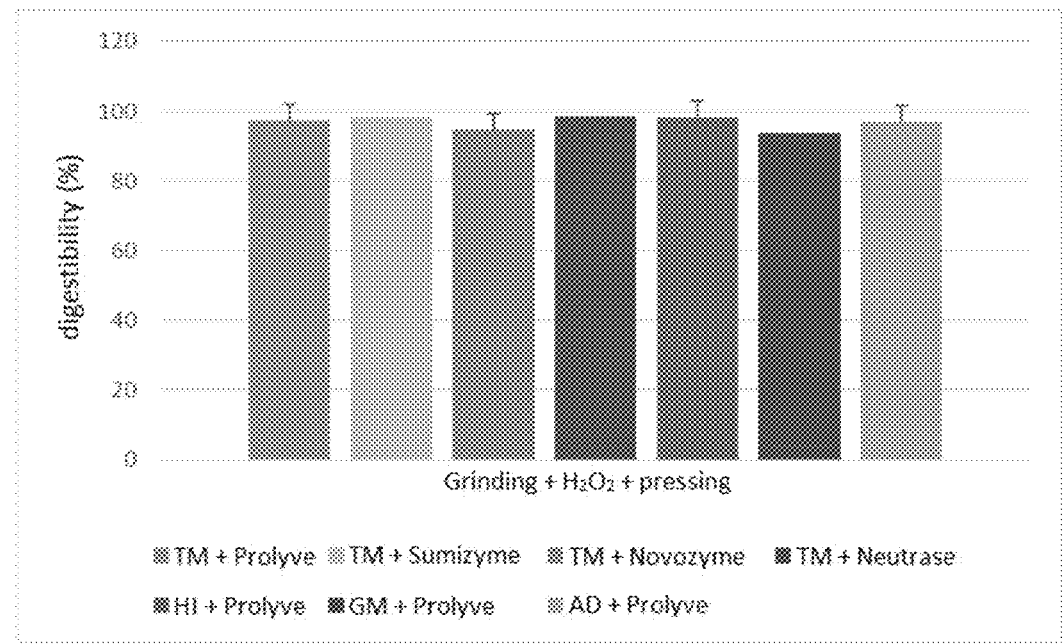

The method makes it possible to obtain a hydrolysate with a very high level of digestibility, >93%, whatever the enzyme or insect studied (FIG. 9).

e) Amino Acid Abundance

The hydrolysate obtained by the method consists predominantly of amino acids such as alanine, glutamate, aspartic acid and tyrosine, and to a lesser extent valine, serine and glycine, whatever the enzyme or insect studied (FIGS. 10-16).

III. Chitin a) Ash

The ash content of the chitin originating from the method "grinding+$H_2O_2$+pressing" was investigated on various insects and different enzymes. These ash contents, stated in % by weight of chitin, are shown in Table 7 below.

TABLE 7

Ash contents of the chitin - different insects and enzymes

| | |
|---|---|
| TM + Prolyve | 0.5 |
| TM + Sumizyme | 0.95 |
| TM + Novozyme | 0.75 |
| TM + Neutrase | 0.65 |
| HI + Prolyve | 2.3 |
| GM + Prolyve | 0.7 |
| AD + Prolyve | 2.35 |

The ash content in the chitin obtained by the method is very low, <2.5%, whatever the enzyme or insect studied.

Figure 17:
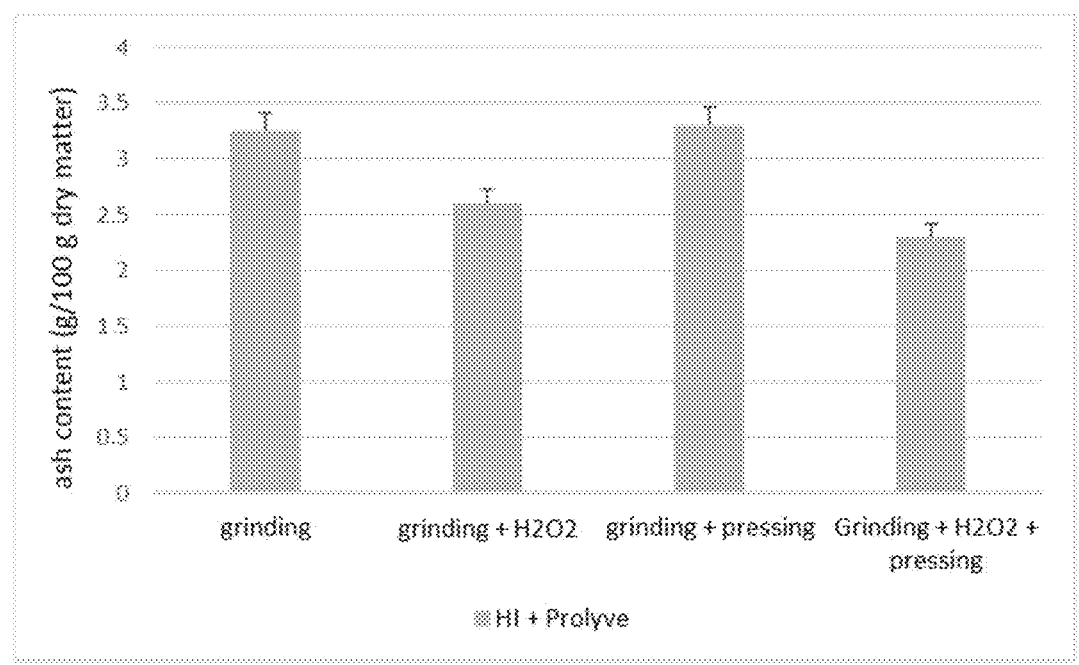

Moreover, an interesting synergy is observed on adding the steps of pressing and of the oxidizing agent on the ash content in the chitin obtained (FIG. 17). Thus, with the method "grinding+$H_2O_2$+pressing" there is demineralization, which can reach 76.2% relative to the method with grinding alone, against demineralization of only 66.7% for a method "grinding+pressing" and 63.5% for a method "grinding+$H_2O_2$".

b) Lipid Content

The lipid content in the chitin obtained by the method is very low, <6.5%, whatever the insect or enzyme used (Table 8), and even <3.2% in the case of *T. molitor*, whatever the enzyme used.

TABLE 8

Lipid content in the chitin

| | |
|---|---|
| TM + Prolyve | 3.1 |
| TM + Sumizyme | 2.8 |
| TM + Novozyme | 2.05 |
| TM + Neutrase | 2.5 |
| GM + Prolyve | 6.3 |
| AD + Prolyve | 6 |

Figure 18:
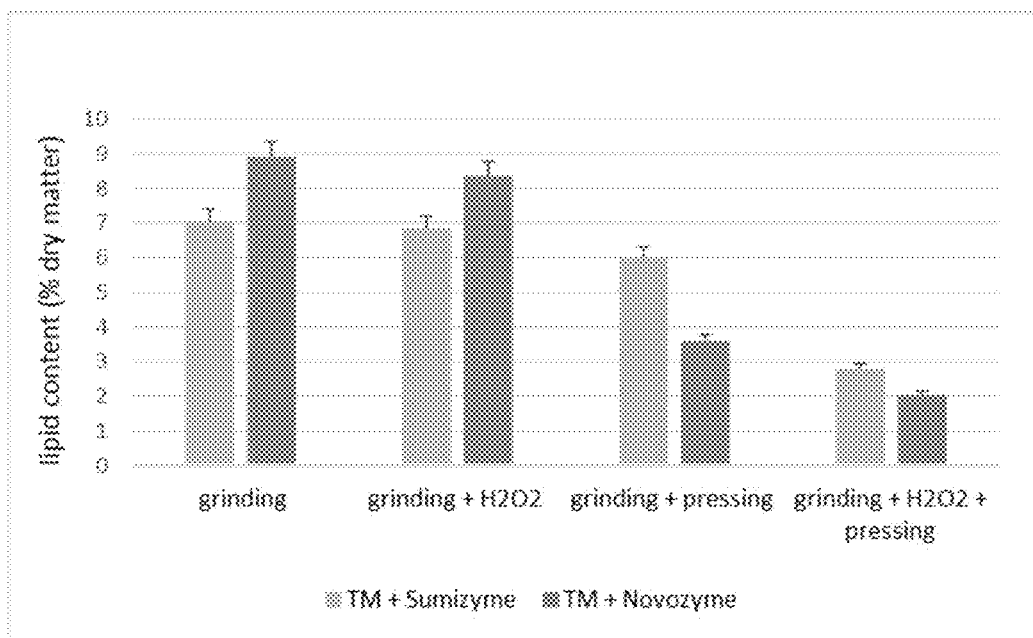

Moreover, an interesting synergy is observed on combining the steps of addition of oxidizing agent and pressing (FIG. 18). In fact, in this case a decrease in the lipid content is observed of 60-77%, against 15-60% in a method with pressing alone and 3-3.6% in the method with the addition of oxidizing agent alone.

c) Content and Abundance of Amino Acids

The amino acid content present in the chitin is relatively low, <46%, whatever the enzyme or insect studied (Table 9).

TABLE 9

Amino acids content present in the chitin

| | |
|---|---|
| TM + Prolyve | 22.75 |
| TM + Sumizyme | 44.74 |
| TM + Novozyme | 45.45 |
| TM + Neutrase | 45.20 |
| HI + Prolyve | 12.97 |
| GM + Prolyve | 18.92 |
| AD + Prolyve | 45.56 |

It can be stated that for all the insects, alanine, tyrosine and proline, and to a lesser extent valine, glycine, leucine and serine are the main amino acids attached to chitin, their content being on average between 15 and 35% of the total amino acids (FIGS. 19-25).

d) Gravimetric Purity

Figure 26:
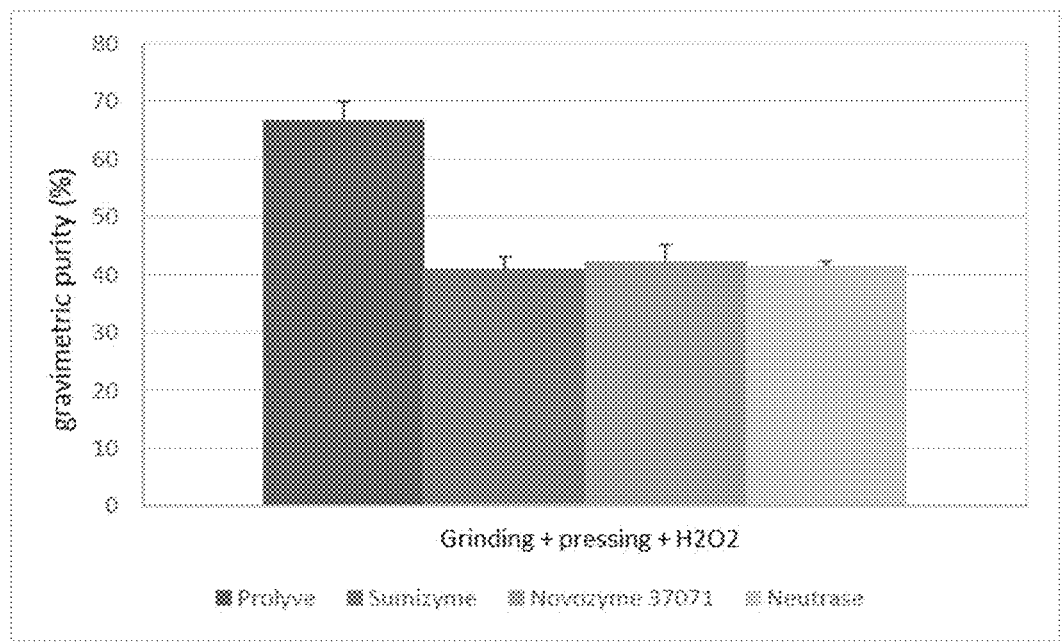
Figure 27:
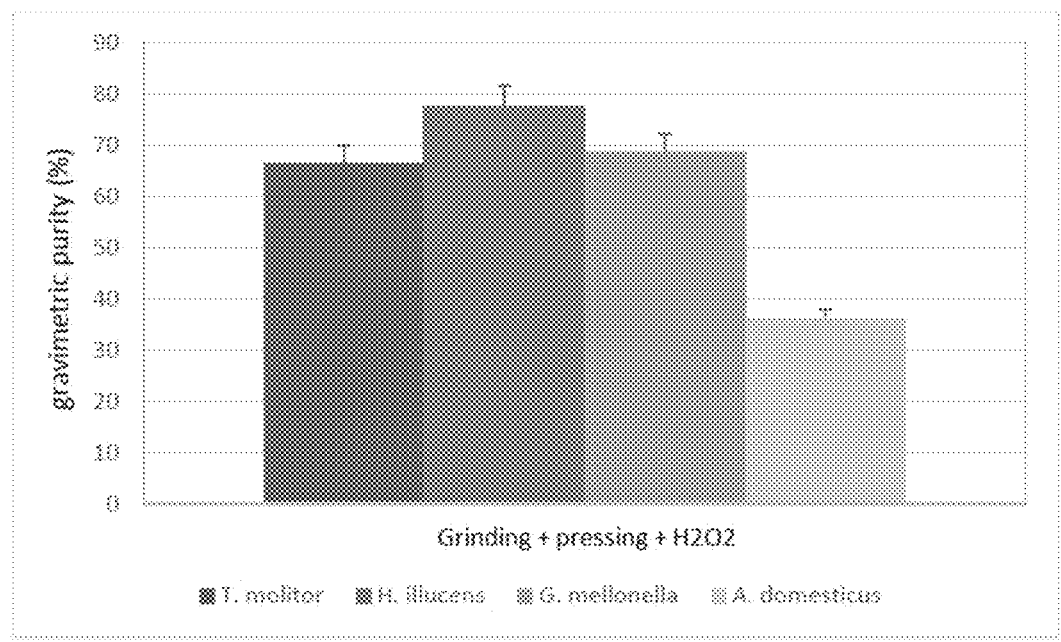

The gravimetric purity of the chitin thus obtained is >36%, whatever the insect and even >40%, whatever the enzyme in the case of *T. molitor* (FIGS. 27 and 26).

e) Colorimetric Purity

Figure 28:
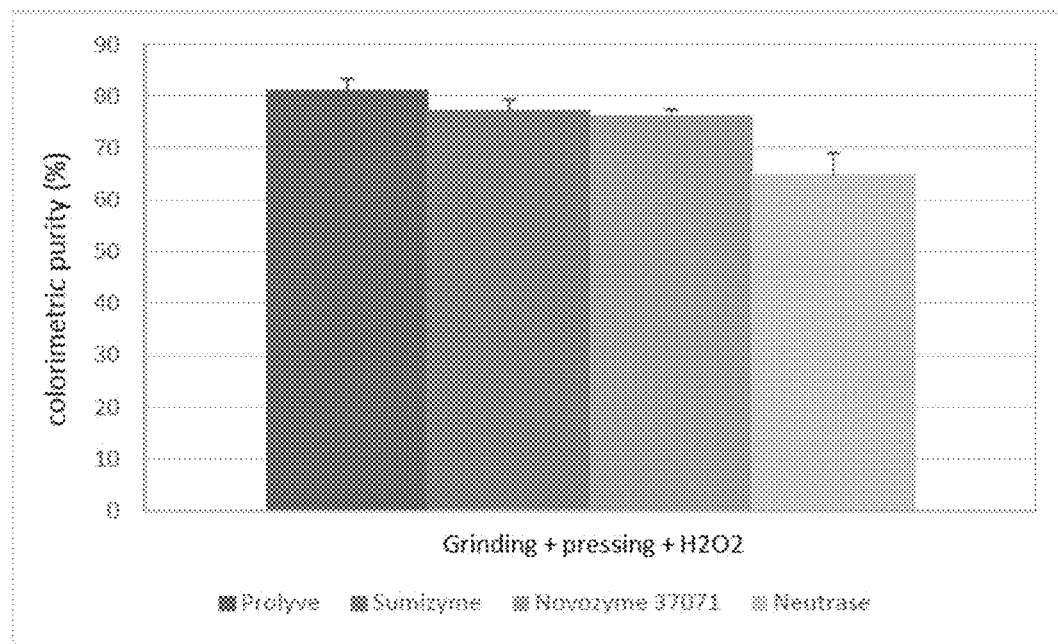
Figure 29:

Combining the steps of adding an oxidizing agent and pressing contributes to a relatively high colorimetric purity of the product obtained, 62-81% whatever the enzyme or insect used (FIGS. 28 and 29).

f) Purity by Difference

Figure 30:
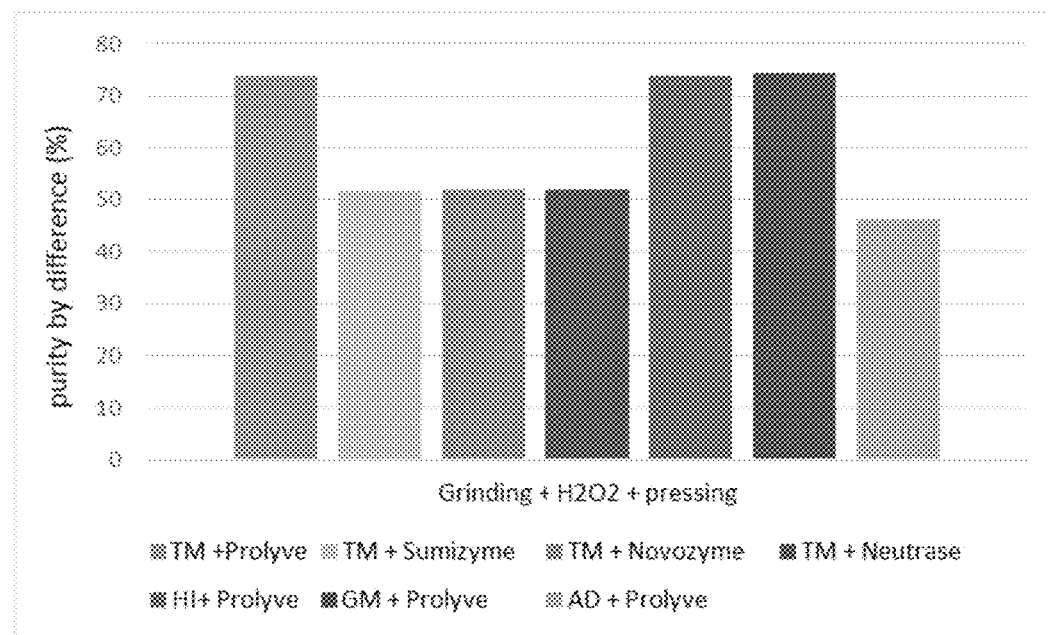
Figure 31:
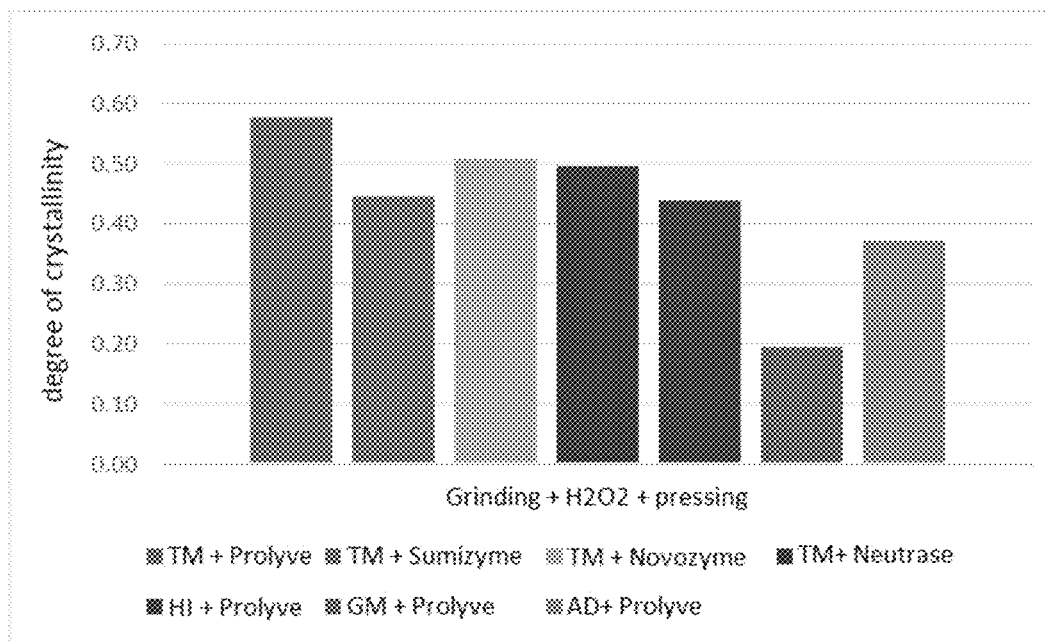

The purity by difference of the products obtained is relatively high, >46%, whatever the insects and enzymes considered, and even >51% in the case of *T. molitor*, and it can even reach 73% in the case *T. molitor*+Prolyve (FIG. 30).

g) Degree of Crystallinity

Treatment with an oxidizing agent tends to make chitin more amorphous (FIG. 31), whatever the insect studied. The degree of crystallinity, i.e. the ratio of the crystalline and amorphous areas of the chitin obtained is between 0.19 and 0.58, and even between 0.45 and 0.58 in the case of *T. molitor*.

The invention claimed is:

1. A method for the production of chitin and/or chitosan from insect cuticles, comprising the following steps in the following order:
   (i) grinding the insect cuticles,
   (ii) pressing the insect cuticles, then
   (iii) enzymatically hydrolyzing the insect cuticles with a proteolytic enzyme, wherein the cuticles are treated with an oxidizing agent before the pressing step.

2. The method according to claim 1, wherein the proteolytic enzyme is a protease.

3. The method according to claim 1, wherein the oxidizing agent is selected from the group consisting of hydrogen peroxide, potassium permanganate, ozone, and sodium hypochlorite.

4. The method according to claim 1, further comprising a step of killing the insects prior to the pressing step.

5. The method according to claim 1, further comprising a step of killing the insects via scalding prior to the pressing step.

6. The method according to claim 1, further comprising a step of killing the insects prior to the pressing step, and wherein the treatment of the cuticles with an oxidizing agent is carried out concomitantly and/or after the killing step.

7. The method according to claim 1, wherein the insect or insects is/are selected from the group consisting of the Coleoptera, the Lepidoptera, the Orthoptera, and the Diptera.

8. A method for the production of chitin from insects, comprising the following steps in the following order:
   a) killing the insects,
   b) grinding the insects to obtain insect cuticles,
   c) pressing the insect cuticles,
   d) enzymatically hydrolyzing the insect cuticles with a proteolytic enzyme,
   e) recovering chitin,
   wherein the insect cuticles are treated with an oxidizing agent before step c).

9. A method for the production of chitosan from insects, comprising the following steps in the following order:
   a) killing the insects,
   b) grinding the insects to obtain insect cuticles,
   c) pressing the insect cuticles,
   d) enzymatically hydrolyzing the insect cuticles with a proteolytic enzyme, e) recovering chitin, f) deacetylating the chitin recovered, g) recovering chitosan, wherein the insect cuticles are treated with an oxidizing agent before step c).

10. The method according to claim 1, wherein the treatment of the cuticles with an oxidizing agent is carried out before, concomitantly, and/or after the grinding step.

11. The method according to claim 1, further comprising a step of killing the insects prior to the pressing and/or grinding step.

12. The method according to claim 1, further comprising a step of killing the insects via scalding prior to the pressing and/or grinding step.

13. The method according to claim 1, further comprising a step of killing the insects prior to the pressing and/or grinding step, wherein the treatment of the cuticles with an oxidizing agent is carried out concomitantly and/or after the killing step.

* * * * *